United States Patent
Waldo

(10) Patent No.: US 7,271,241 B2
(45) Date of Patent: Sep. 18, 2007

(54) DIRECTED EVOLUTION METHODS FOR IMPROVING POLYPEPTIDE FOLDING AND SOLUBILITY AND SUPERFOLDER FLUORESCENT PROTEINS GENERATED THEREBY

(75) Inventor: Geoffrey S. Waldo, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 345 days.

(21) Appl. No.: 10/423,688

(22) Filed: Apr. 24, 2003

(65) Prior Publication Data

US 2004/0078148 A1   Apr. 22, 2004

Related U.S. Application Data

(63) Continuation-in-part of application No. 10/132,067, filed on Apr. 24, 2002, now abandoned.

(51) Int. Cl.
   *A61K 38/16* (2006.01)
   *C07K 14/00* (2006.01)

(52) U.S. Cl. ..................... 530/350; 435/69.1
(58) Field of Classification Search ................. 530/350
   See application file for complete search history.

(56) References Cited

U.S. PATENT DOCUMENTS

| | | | |
|---|---|---|---|
| 6,307,024 B1 | 10/2001 | Novak et al. | 530/351 |
| 6,414,119 B1 | 7/2002 | Fisher | 530/350 |
| 6,448,087 B1 | 9/2002 | Waldo | 436/86 |
| 2002/0107362 A1 | 8/2002 | Thastrup et al. | 530/350 |
| 2002/0123113 A1 | 9/2002 | Tsien | 534/183 |
| 2002/0177189 A1 | 11/2002 | Bjorn et al. | 435/693.1 |
| 2003/0013849 A1 | 1/2003 | Ward | 530/350 |

FOREIGN PATENT DOCUMENTS

| WO | 0046233 | 8/2000 |
|---|---|---|
| WO | 0123602 | 4/2001 |

OTHER PUBLICATIONS

Stemmer, (1994) Nature 370: 389.
Stemmer, (1994) Proc. Natl. Acad. Sci. USA 91: 10747.
Stemmer, (1995) Biotechnology 13: 549.
Arnold, (1996) Chem. Eng. Sci. 51: 5091.
Zhang et al., (1997) Proc. Natl. Acad. Sci. USA 94: 4504.
Zhao and Arnold (1997) Proc. Natl. Acad. Sci. USA 94: 7997.
Moore et al., (1997) Mol. Biol. 272: 336.
Crameri et al., (1996) Nat. Biotechnol. 14: 315.
Heim et al., (1994) Proc. Natl. Acad. Sci. USA 91: 12501.
Macbeath et al., (1998) Science 279: 1958.
Waldo et al., (1999) Nat. Biotechnol. 17:691.
Ormo et al., (1996) Science Sep. 6: 273(5280):1392.
Yang et al., (1996) Nat. Biotechnol. (1996) Oct; 14(10):1246.
Matz et al., (1999) Nat. Biotechnol. 17: 969.
Yarbrough et al., (2001) Proc. Natl. Acad. Sci. USA 98: 462.
Weihler et al., (2001) FEBS Letters 487: 384.
Terskikh et al., (2000) Science 290: 1585.
Baird et al., (2000) Proc. Natl. Acad. Sci. USA 97: 11984.
Zimmer, (2002) Chem. Rev. 102: 759.
Zhang et al., (2002) Nature Reviews 3: 906.
Ando et al., (2002) Proc. Natl. Acad. Sci. USA 99: 12651.
Weidenmann et al., (2000) Proc. Natl. Acad. Sci. USA 97: 14091.
Tu et al., (2003) Biochem. Biophys. Res. Commun. 301: 879.
Lukyanov et al., (2000) J. Biol. Chem. 275: 25879.
Dove et al., (2001) Coral Reefs 19: 197.
Beddoe et al., (2003) Acta Cryst. D59: 597.
Bulina et al., (2002) BMC Biochem. 3: 7.
Gurskaya et al., (2001) FEBS Letters 507: 16.
Cotlet et al., (2001) Proc. Natl. Acad. Sci. USA 98: 14398.
Crameri et al, (1994) Eur. J. Biochem. 226: 53.
Smith and Waterman, (1981) Adv. Appl. Math 2: 482.
Tsien, (1998) Annu. Rev. Biochem. 67: 509.
Miyawaki et al., (1999) Proc. Natl. Acad. Sci. USA 96: 2135.
Martin et al., (2001) J. Mol. Biol. 309(3): 717.
Bevis and Glick (2002) Nat. Biotechnol. Jan; 20(1): 83.
Campbell et al., (2002) Proc. Natl. Acad. Sci. USA 11;99(12): 7877.
Baird et al., (1999) Proc. Natl. Acad. Sci. USA 96: 11241.

*Primary Examiner*—Michael Borin
(74) *Attorney, Agent, or Firm*—Kenneth K. Sharples

(57) ABSTRACT

The current invention provides methods of improving folding of polypeptides using a poorly folding domain as a component of a fusion protein comprising the poorly folding domain and a polypeptide of interest to be improved. The invention also provides novel green fluorescent proteins (GFPs) and red fluorescent proteins that have enhanced folding properties.

18 Claims, 11 Drawing Sheets

SEQUENCE LISTING

<160> NUMBER OF SEQ ID NOS: 42

<210> SEQ ID NO 1
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 1
gatataacta gtaatgggca caaattttct gtcagagga                    39

<210> SEQ ID NO 2
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 2
gatataacta gtaatgggca caaattttct gtcagtgga                    39

<210> SEQ ID NO 3
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 3
tacttcggta ccattaacat caccatctaa ttcaacaag                    39

<210> SEQ ID NO 4
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 4
gatataacta gtaacggaaa actcaccctt aaatttatt                    39

<210> SEQ ID NO 5
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 5
gatataacta gttacggaaa actcaccctt aaatttatt                    39

```
<210> SEQ ID NO 6
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 6
tacttcggta ccgtttgtag catcaccttc accctctcc                              39

<210> SEQ ID NO 7
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 7
tacttcggta ccgtatgtag catcaccttc accctctcc                              39

<210> SEQ ID NO 8
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 8
gatataacta gtggaaaact acctgttcca tggccaaca                              39

<210> SEQ ID NO 9
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 9
tacttcggta cctccagtag tgcaaataaa tttaagggt                              39

<210> SEQ ID NO 10
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 10
gatataacta gtggttatgt acaggaacgc actatatct                              39

<210> SEQ ID NO 11
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 11
tacttcggta ccaccttcgg gcatggcact cttgaaaaa                              39

<210> SEQ ID NO 12
<211> LENGTH: 39
<212> TYPE: DNA
<213> ORGANISM: Artificial sequence
<220> FEATURE:
<223> OTHER INFORMATION: Chemically Synthesized; Synthetic Primer
```

```
<400> SEQUENCE: 12
gatataacta gtgatgacgg gacctacaag acgcgtgct                              39

<210> SEQ ID NO 13
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 13
gatataacta gtgatgacgg gaactacaag acgcgtgct                              39

<210> SEQ ID NO 14
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 14
tacttcggta ccatctttga aagatatagt gcgttcctg                              39

<210> SEQ ID NO 15
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 15
gatataacta gtgataccct tgttaatcgt atcgagtta                              39

<210> SEQ ID NO 16
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 16
tacttcggta ccatcacctt caaacttgac ttcagcacg                              39

<210> SEQ ID NO 17
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 17
gatataacta gtgattttaa agaagatgga aacattctc                              39

<210> SEQ ID NO 18
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 18
tacttcggta ccatcaatac cttttaactc gatacgatt                              39
```

<210> SEQ ID NO 19
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 19
gatataacta gtaaactcga gtacaacttt aactcacac                         39

<210> SEQ ID NO 20
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 20
gatataacta gtaaactcga gtacaactat aactcacac                         39

<210> SEQ ID NO 21
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 21
tacttcggta cctttgtgtc cgagaatgtt tccatcttc                         39

<210> SEQ ID NO 22
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 22
gatataacta gttttaactc acacaatgta tacatcacg                         39

<210> SEQ ID NO 23
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 23
gatataacta gttataactc acacaatgta tacatcacg                         39

<210> SEQ ID NO 24
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 24
tacttcggta ccaaagttgt actcgagttt gtgtccgag                         39

<210> SEQ ID NO 25
<211> LENGTH: 39
<212> TYPE: DNA
<213> ORGANISM: Artificial sequence
<220> FEATURE:
<223> OTHER INFORMATION: Chemically Synthesized; Synthetic Primer

```
<400> SEQUENCE: 25
tacttcggta ccatagttgt actcgagttt gtgtccgag                              39

<210> SEQ ID NO 26
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 26
gatataacta gtcaaaagaa tggaatcaaa gctaacttc                              39

<210> SEQ ID NO 27
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 27
tacttcggta ccttgtttgt ctgccgtgat gtatacatt                              39

<210> SEQ ID NO 28
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 28
gatataacta gtgatggttc cgttcaacta gcagaccat                              39

<210> SEQ ID NO 29
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 29
tacttcggta ccatcttcaa cgttgtggcg aattttgaa                              39

<210> SEQ ID NO 30
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 30
tacttcggta ccatcttcaa tgttgtggcg aattttgaa                              39

<210> SEQ ID NO 31
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 31
gatataacta gtggcgatgg ccctgtcctt ttaccagac                              39
```

```
<210> SEQ ID NO 32
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 32
tacttcggta ccgccaattg gagtattttg ttgataatg                              39

<210> SEQ ID NO 33
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 33
gatataacta gtttaccaga caaccattac ctgtcgaca                              39

<210> SEQ ID NO 34
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 34
tacttcggta cctaaaagga cagggccatc gccaattgg                              39

<210> SEQ ID NO 35
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 35
gatataacta gtaagcgtga ccacatggtc cttcttgag                              39

<210> SEQ ID NO 36
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 36
tacttcggta ccctttttcgt tgggatcttt cgaaaggac                             39

<210> SEQ ID NO 37
<211> LENGTH: 39
<212> TYPE: DNA
<213> ORGANISM: Artificial sequence
<220> FEATURE:
<223> OTHER INFORMATION: Chemically Synthesized; Synthetic Primer

<400> SEQUENCE: 37
tacttcggta ccctttttcgt tgggatcttt cgaaagggc                             39

<210> SEQ ID NO 38
<211> LENGTH: 717
<212> TYPE: DNA
<213> ORGANISM: Aequorea victoria
```

<400> SEQUENCE: 38

```
atgagcaaag gagaagaact tttcactgga gttgtcccaa ttcttgttga attagatggt      60
gatgttaatg ggcacaaatt ttctgtcagt ggagagggtg aaggtgatgc tacatacgga     120
aaactcaccc ttaaatttat ttgcactact ggaaaactac ctgttccatg gccaacactt     180
gtcactactc tgacctatgg tgttcaatgc ttttcccgtt atccggatca catgaaacgg     240
catgactttt tcaagagtgc catgcccgaa ggttatgtac aggaacgcac tatatctttc     300
aaagatgacg ggaactacaa gacgcgtgct gaagtcaagt ttgaaggtga taccttgtt      360
aatcgtatcg agttaaaagg tattgatttt aagaagatg aaacattct cggacacaaa       420
ctcgagtaca actataactc acacaatgta tacatcacgg cagacaaaca aaagaatgga     480
atcaaagcta acttcaaaat tcgccacaac attgaagatg gttccgttca actagcagac     540
cattatcaac aaaatactcc aattggcgat ggccctgtcc ttttaccaga caaccattac     600
ctgtcgacac aatctgccct ttcgaaagat cccaacgaaa agcgtgacca catggtcctt     660
cttgagtttg taactgctgc tgggattaca catggcatgg atgagctcta caaataa       717
```

<210> SEQ ID NO 39
<211> LENGTH: 238
<212> TYPE: PRT
<213> ORGANISM: Aequorea victoria

<400> SEQUENCE: 39

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 40
<211> LENGTH: 678
<212> TYPE: DNA
<213> ORGANISM: Discosoma sp.

<400> SEQUENCE: 40

```
atggagtctt ccgaggatgt tatcaaggag ttcatgaggt ttaaggttca catggaagga      60
tcggtcaatg ggcacgagtt tgaaatagaa ggcgaaggag aggggaggcc atacgaaggc     120
acccagaacg taaagcttaa ggtaactaag ggggacctt tgccatttgc ttgggatatt      180
ttgtcaccac aatttcagta tggaagcaag gtatatgtca agcaccctgc cgacatacca     240
gactataaaa agctgtcatt tcctgaagga tttaaatggg aaagggtcat gaactttgaa     300
gacggtggcg tcgctactgt aacccaggat ccagtttgg aggatggctg tttgatctac      360
aaggtcaagt tcattggcgt gaactttcct tccgatggac ctgttatgca aaagaagaca     420
atgggctggg aaccgagcac tgagcgtttg tatcctcgtg atggcgtgtt gaaaggagat     480
attcataagg ctctgaagct gaaagacggt ggtcattacc tagttgatat caaaagtatt     540
tacatggcaa agaagcctgt gcagctacca gggtactact atgttgactc caaactggat     600
ataacaaacc acaacgaaga ctatacaatc gttgagcagt atgaaagagc cgagggacgc     660
caccatctgt cctttaa                                                    678
```

<210> SEQ ID NO 41
<211> LENGTH: 225
<212> TYPE: PRT
<213> ORGANISM: Discosoma sp.

<400> SEQUENCE: 41

```
Met Glu Ser Ser Glu Asp Val Ile Lys Glu Phe Met Arg Phe Lys Val
1               5                   10                  15

His Met Glu Gly Ser Val Asn Gly His Glu Phe Glu Ile Glu Gly Glu
            20                  25                  30

Gly Glu Gly Arg Pro Tyr Glu Gly Thr Gln Asn Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Ala Thr Val Thr Gln Asp Ser Ser
            100                 105                 110

Leu Glu Asp Gly Cys Leu Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Pro Ser Thr Glu Arg Leu Tyr Pro Arg Asp Gly Val Leu Lys Gly Asp
145                 150                 155                 160

Ile His Lys Ala Leu Lys Leu Lys Asp Gly Gly His Tyr Leu Val Asp
                165                 170                 175

Ile Lys Ser Ile Tyr Met Ala Lys Lys Pro Val Gln Leu Pro Gly Tyr
            180                 185                 190

Tyr Tyr Val Asp Ser Lys Leu Asp Ile Thr Asn His Asn Glu Asp Tyr
        195                 200                 205
```

-continued

```
Thr Ile Val Glu Gln Tyr Glu Arg Ala Glu Gly Arg His His Leu Phe
    210             215             220
Leu
225

<210> SEQ ID NO 42
<211> LENGTH: 238
<212> TYPE: PRT
<213> ORGANISM: Aequorea victoria

<400> SEQUENCE: 42

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

DIRECTED EVOLUTION METHODS FOR IMPROVING POLYPEPTIDE FOLDING AND SOLUBILITY AND SUPERFOLDER FLUORESCENT PROTEINS GENERATED THEREBY

RELATED APPLICATIONS

This patent application is a continuation-in-part of U.S. patent application Ser. No. 10/132,067, filed Apr. 24, 2002 now abandoned.

STATEMENT AS TO RIGHTS TO INVENTIONS MADE UNDER FEDERALLY SPONSORED RESEARCH OR DEVELOPMENT

This invention was made with government support under Contract No.W-7405-ENG-36 awarded by the U.S. Department of Energy. The government has certain rights in the invention.

BACKGROUND OF THE INVENTION

Protein insolubility constitutes a significant problem in basic and applied bioscience, in many situations limiting the rate of progress in these areas. Protein folding and solubility has been the subject of considerable theoretical and empirical research. However, there still exists no general method for improving intrinsic protein solubility. Such a method would greatly facilitate protein structure-function studies, drug design, de novo peptide and protein design and associated structure-function studies, industrial process optimization using bioreactors and microorganisms, and many disciplines in which a process or application depends on the ability to tailor or improve the solubility of proteins, screen or modify the solubility of large numbers of unique proteins about which little or no structure-function information is available, or adapt the solubility of proteins to new environments when the structure and function of the protein(s) are poorly understood or unknown.

Overexpression of cloned genes using an expression host, for example *E. coli*, is the principal method of obtaining proteins for most applications. Unfortunately, many such cloned foreign proteins are insoluble or unstable when overexpressed. There are two sets of approaches currently in use which deal with such insoluble proteins. One set of approaches modifies the environment of the protein in vivo and/or in vitro. For example, proteins may be expressed as fusions with more soluble proteins, or directed to specific cellular locations. Chaperons may be coexpressed to assist folding pathways. Insoluble proteins may be purified from inclusion bodies using denaturants and the protein subsequently refolded in the absence of the denaturant. Modified growth media and/or growth conditions can sometimes improve the folding and solubility of a foreign protein. However, these methods are frequently cumbersome, unreliable, ineffective, or lack generality. A second set of approaches changes the sequence of the expressed protein. Rational approaches employ site-directed mutation of key residues to improve protein stability and solubility. Alternatively, a smaller, more soluble fragment of the protein may be expressed. These approaches require a priori knowledge about the structure of the protein, knowledge which is generally unavailable when the protein is insoluble. Furthermore, rational design approaches are best applied when the problem involves only a small number of amino-acid changes. Finally, even when the structure is known, the changes required to improve solubility may be unclear. Thus, many thousands of possible combinations of mutations may have to be investigated leading to what is essentially an "irrational" or random mutagenesis approach. Such an approach requires a method for rapidly determining the solubility of each version.

Random or "irrational" mutagenesis redesign of protein solubility carries the possibility that the native function of the protein may be destroyed or modified by the inadvertent mutation of residues which are important for function, but not necessarily related to solubility. However, protein solubility is strongly influenced by interaction with the environment through surface amino acid residues, while catalytic activities and/or small substrate recognition often involve partially buried or cleft residues distant from the surface residues. Thus, in many situations, rational mutation of proteins has demonstrated that the solubility of a protein can be modified without destroying the native function of the protein. Modification of the function of a protein without effecting its solubility has also been frequently observed. Furthermore, spontaneous mutants of proteins bearing only 1 or 2 point mutations have been serendipitously isolated which have converted a previously insoluble protein into a soluble one. This suggests that the solubility of a protein can be optimized with a low level of mutation and that protein function can be maintained independently of enhancements or modifications to solubility. Furthermore, a screen for function may be applied concomitantly after each round of solubility selection during the directed evolution process.

In the absence of a screen for function, for example when the function is unknown, the final version of the protein can be backcrossed against the wild type in vitro to remove nonessential mutations. This approach has been successfully applied by Stemmer in "Rapid Evolution Of A Protein In Vitro By DNA Shuffling," by W. P. C. Stemmer, Nature 370, 389 (1994), and in "DNA Shuffling By Random Fragmentation And Reassembly: In Vitro Recombination For Molecular Evolution," by W. P. C. Stemmer, Proc. Natl. Acad. Sci. USA 91, 10747 (1994) to problems in which the function of a protein had been optimized and it was desired to remove nonessential mutations accumulated during directed evolution. The development of highly specialized protein variants by directed, in vitro evolution, which exerts unidirectional selection pressure on organisms, is further discussed in: "Searching Sequence Space: Using Recombination To Search More Efficiently And Thoroughly Instead Of Making Bigger Combinatorial Libraries," by Willem P. C. Stemmer, Biotechnology 13, 549 (1995); in "Directed Evolution: Creating Biocatalysts For The Future," by Frances H. Arnold, Chemical Engineering Science 51, 5091 (1996); in "Directed Evolution Of A Fucosidase From A Galactosidase By DNA Shuffling And Screening," by Ji-Hu Zhang et al., Proc. Natl. Acad. Sci. USA 94, 4504 (1997); in "Functional And Nonfunctional Mutations Distinguished By Random Combination Of Homologous Genes," by Huimin Zhao and Frances H. Arnold, Proc. Natl. Acad. Sci. USA 94, 7007 (1997); and in "Strategies For The In Vitro Evolution of Protein Function: Enzyme Evolution By Random Recombination of Improved Sequences", by Jeff Moore et al., J. Mol. Biol. 272, 336-346 (1997). Therein, efficient strategies for engineering new proteins by multiple generations of random mutagenesis and recombination coupled with screening for improved variants is described. However, there are no teachings concerning the use of directed evolutionary processes to improve solubility of proteins; rather, the mutagenesis was directed to improvement of protein function. It should be mentioned, however, that in order for the protein to function properly in any environment, it must at least be correctly folded.

Finally, for structural determination it is often not necessary or even desirable to have a fully functional version of the protein. If the mutational rate is low (ensured by molecular backcrossing), it is likely that the structure of the wild-type and solubility optimized versions of a protein will be similar. As long as the protein is soluble, and a structure can be obtained, it should then be possible to redesign the solubility of the protein using rational methods, if desired.

Wild type green fluorescent protein (GFP) cloned from *Aequorea Victoria*, normally misfolds and is poorly fluorescent when overexpressed in the heterologous host *E. coli*. It is found predominantly in the inclusion body fraction of cell lysates. The misfolding is incompletely understood, but is thought to result from the increased expression level or rate in *E. coli*, or the inadequacy of the bacterial chaperone and related folding machinery under conditions of overexpression. The folding yield also decreases dramatically at higher temperatures (37° C. vs. 27° C.). This wild type GFP is a very poor folder, as it is extremely sensitive to the expression environment.

Green fluorescent protein has become a widely used reporter of gene expression and regulation. DNA shuffling has been used to obtain a mutant having a whole cell fluorescence 45-times greater than the standard, commercially available plasmid GFP. See, e.g., "Improved Green Fluorescent Protein By Molecular Evolution Using DNA Shuffling," by Andreas Crameri et al., Nature Biotechnology 14, 315 (1996). The screening process optimizes the function of GFP (green fluorescence), and thus uses a functional screen. Although the screening process coincidentally optimizes the solubility of the GFP, in that the GFP is only fluorescent when properly folded, there is no mention of using soluble GFP as a tag to monitor solubility of other proteins; that is, the function of the protein and not its solubility are being modified. In "Wavelength Mutations And Post-translational Auto-oxidation Of Green Fluorescent Protein," by Roger Heim et al., Proc. Natl. Acad. Sci. USA 91, 12501 (1994), GFP was mutagenized and screened for variants with altered absorption or emission spectra. The authors mention that in place of proteins labeled with fluorescent tags to detect location and sometimes their conformational changes both in vitro and in intact cells, a possible strategy would be to concatenate the gene for the nonfluorescent protein of interest with the gene for a naturally fluorescent protein and express the fusion product. However, the focus of this paper is the extension of the usefulness of GFP by enabling visualization of differential gene expression and protein localization and measurement of protein association by fluorescence resonance energy transfer, by making available two visibly distinct colors. There is no mention of the use of the gene construct for solubility determinations. The paper further discusses the expression of GFP in *E. coli* under the control of a T7 promoter, and that the bacteria contained inclusion bodies consisting of protein indistinguishable from jellyfish or soluble recombinant protein on denaturing gels, but that this material was completely nonfluorescent, lacked the visible absorbance bands of the chromophore, and did not become fluorescent when solubilized and subjected to protocols that renature GFP, as opposed to the soluble GFP in the bacteria which undergoes correct folding and, therefore, fluoresces.

Chun Wu et al. in "Novel Green Fluorescent Protein (GFP) Baculovirus Expression Vectors," Gene 190, 157 (1997), describe the construction of Baculovirus expression vectors which contain GFP as a reporter gene. The authors follow the production and purification of a protein of interest by in-frame cloning of the gene that expresses the protein in insect cells with the GFP open reading frame, thereby permitting visualization of the produced GFP-fusion protein using UV light. However, the purified GFP-XylE fusion protein was found to be insoluble after harvest. The authors did not correlate the level of fluorescence of the cells expressing the GFP-XylE fusion protein with the solubility of cells expressing the XylE protein alone. Therefore, this reference does not teach the use of the fusion protein fluorescence as an indicator of the solubility of the specific protein XylE or of the solubility of other proteins.

In "Application Of A Chimeric Green Protein Fluorescent Protein To Study Protein-Protein Interactions," by N. Garamszegi et al., Biotechniques 23, 864 (1997), the authors discuss the fusion between GFP and human calmodulin-like protein (CLP) and show that this protein retains fluorescence and the known characteristics of CLP. That is, the GFP portion remains responsible for efficient fluorescent signals with little or no influence on the properties of the fused protein of interest. The authors maintain that the exhibited GFP fluorescence provides information concerning the maintenance of the GFP structural integrity in the chimeric protein, but does not provide information about the integrity of the entire fusion protein and, in particular, does not allow any statements concerning the maintenance of CLP function or integrity. From these statements, it is clear that this paper does not contemplate the use of the GFP as a solubility reporter for the CLP.

It has been demonstrated that improving the apparent functionality of a protein can sometimes increase the concomitant solubility of the protein, as in: "Redesigning enzyme topology by directed evolution," by G. Macbeath, P. Kast, and D Hilvert, Science 279, 1958-1961 (1998); "Expression of an antibody fragment at high levels in the bacterial cytoplasm," by P. Martineau, P. Jones, and G. Winter, J. Mol. Biol. 280, 117-127 (1998); "Antibody scFv fragments without disulfide bonds made by molecular evolution," K. Proba, A. Worn, A. Honegger, and A. Pluckthun, J. Mol. Biol. 275, 245-253 (1998); and "Functional Expression of Horseradish Peroxidase in *E. coli* by Directed Evolution," Lin Zhanglin, Todd Thorsen, and Frances H. Arnold, Biotechnol. Prog. 15, 467-471 (1999). In each case, the driving force for the directed evolution was the functionality of the protein of interest. For example, if the protein was an enzyme, the assay for improved function was the turnover of a chromogenic analog of the enzyme's natural substrate; if the protein was an antibody, it was the recognition of the target antigen by the antibody.

For cytoplasmic expression of antibodies, the recognition was linked to cell survival, (binding of the antibody to a selectable protein marker which was an antigen for the antibody of interest providing selection for functional antibodies); in the case of phage displayed antibodies without disulfide bonds, the recognition was transduced to successful binding of the displayed phage to the target antigen of the displayed antibody in a biopanning protocol. An apparent increase in the amount of protein expressed in the soluble fraction relative to the unselected target proteins was noted upon expression of the proteins in *E. col*. The apparent increase in activity of desirable mutants during the evolution was due at least in part to an increase in the number of correctly folded (and hence functional) protein molecules, and not exclusively to an increase in the specific activity of a given protein molecule. However, the driving force for the selection or screening process during the directed evolution depended on the functionality (and functional assay for) the protein of interest.

Many proteins have no easily detectable functional assay, and thus identification of proteins with improved folding yield by an increase in apparent activity due to a larger number of correctly folded molecules, is not a general method for improving folding by directed evolution. Furthermore, even when functional assays are available, apparent increases in activity can also be due to increases in the specific activity (activity of an individual protein molecule) even when the total number of correctly folded molecules remains the same. Thus, increases in apparent activity do not necessarily translate to increases in the solubility of proteins. Furthermore, functional assays are protein-specific, and thus must be developed on a case-by-case basis for each new protein. Functional assays therefore lack the generality needed to identify proteins which are soluble, or to find genetic variants (mutants and fragments) of proteins with improved solubility, in a high-throughput manner for proteomics or functional genomics wherein large numbers of different proteins about which little or no functional/structural information is known, are to be solubly expressed.

Stemmer and coworkers applied directed evolution to screen for mutants or variants of GFP that exhibited increased fluorescence and folding yield in *E. coli* (see, e.g., Crameri et al., *Nat. Biotechnol.* 143:315-319, 1996). They identified a mutant that exhibited increased folding ability. This version of GFP, termed cycle-3 or GFP3 contains the mutations F99S, M153T and V163A. GFP3 is relatively insensitive to the expression environment and folds well in a wide variety of hosts, including *E. coli*. GFP3 folds equally well at 27° C. and 37° C. Thus, the GFP3 mutations also appear to eliminate potential temperature sensitive folding intermediates that occur during folding of wild type GFP.

GFP3 can be made to misfold by expression as a fusion protein with another poorly folded polypeptide. GFP3 has been used to report on the "folding robustness" of N-terminally fused proteins during expression in *E. coli* (Waldo et al., *Nat. Biotechnol.* 17:691-695, 1999). If test protein, Xi, misfolds and is insoluble when expressed in *E. coli*, cells expressing the corresponding fusion protein Xi-L-GFP3 (where L is a small flexible linker) are poorly fluorescent, indicating the high probability of failure of the GFP3 to fold and become fluorescent. On the other hand, when protein Xs folds well and is highly soluble when expressed in *E. col*, cells expressing the corresponding fusion protein Xs-L-GFP3 are highly fluorescent, indicating the successful folding of the GFP3 domain. These observations suggest the presence of latent folding defects in the folding trajectory of GFP3 and that poorly folded fused polypeptides effectively 'bait' the GFP3 to misfold.

This aspect of GFP3 folding has been used to evolve soluble versions of proteins that normally misfold and aggregate when expressed in *E. coli*. This methodology is described, for example, in WO 01/23602. In these methods, the sequence of the reporter, e.g., GFP3 domain, remains constant and a poorly folded upstream domain is mutated. Better folded variants of domain X are identified by increased fluorescence.

BRIEF SUMMARY OF THE INVENTION

The present invention provides directed evolution methods for improving the folding and solubility characteristics of polypeptides. A number of fluorescent proteins having improved solubility and folding characteristics are provided, including superfolder GFP and DsRed fluorescent proteins.

The superfolder (right) has a higher proportion of soluble protein compared to the cycle-3 redshift (left), consistent with the improved folding of superfolder GFP.

Figure 6:
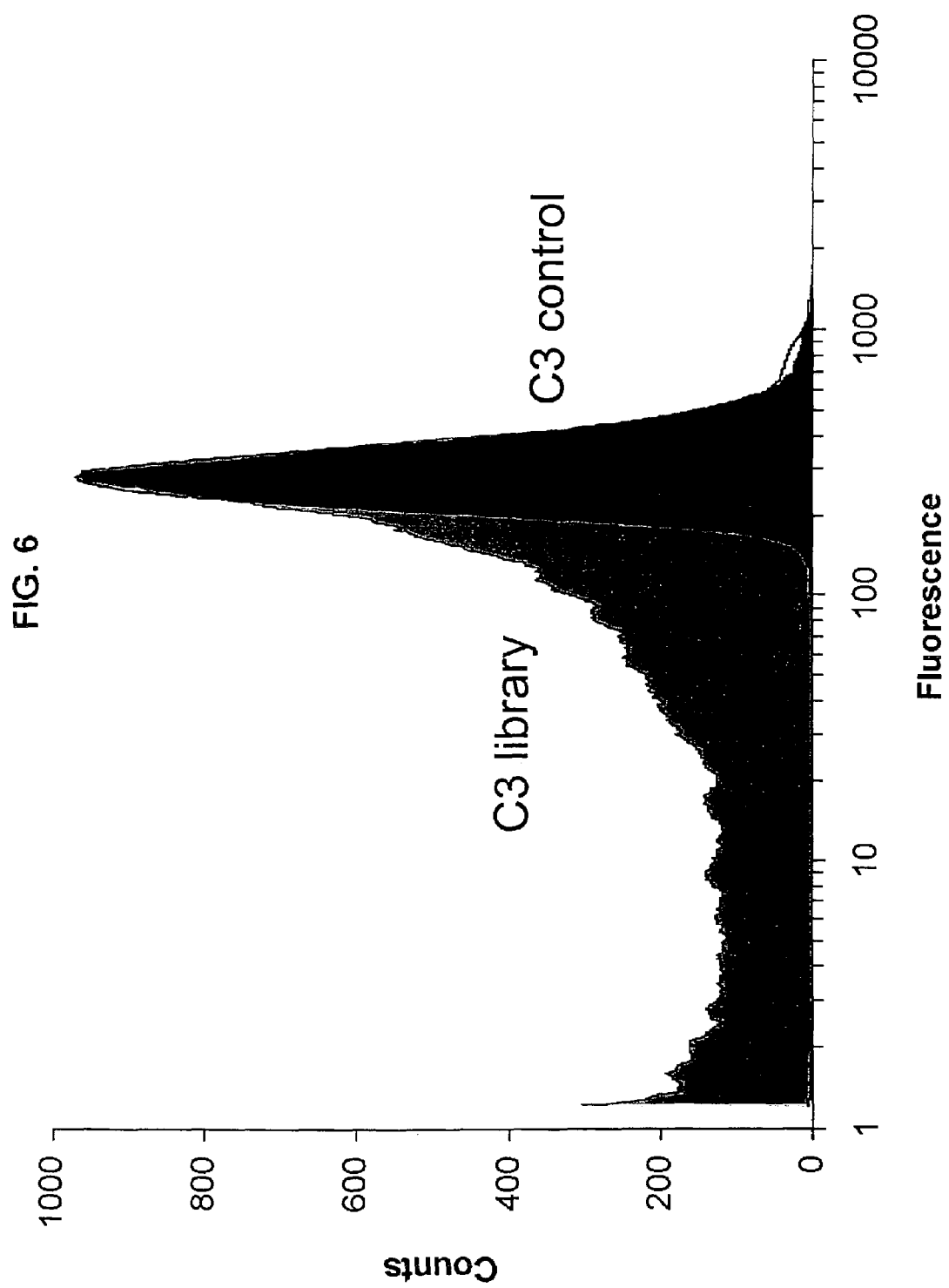

FIG. 6. Flow cytometric analyses of cycle-3 redshift mutant pool library (grey) or control parental cycle-3 redshift (dark grey). Number of events (cells) y-axis; fluorescence intensity of each event (x-axis). Note the logarithmic fluorescence scale.

Figure 7:
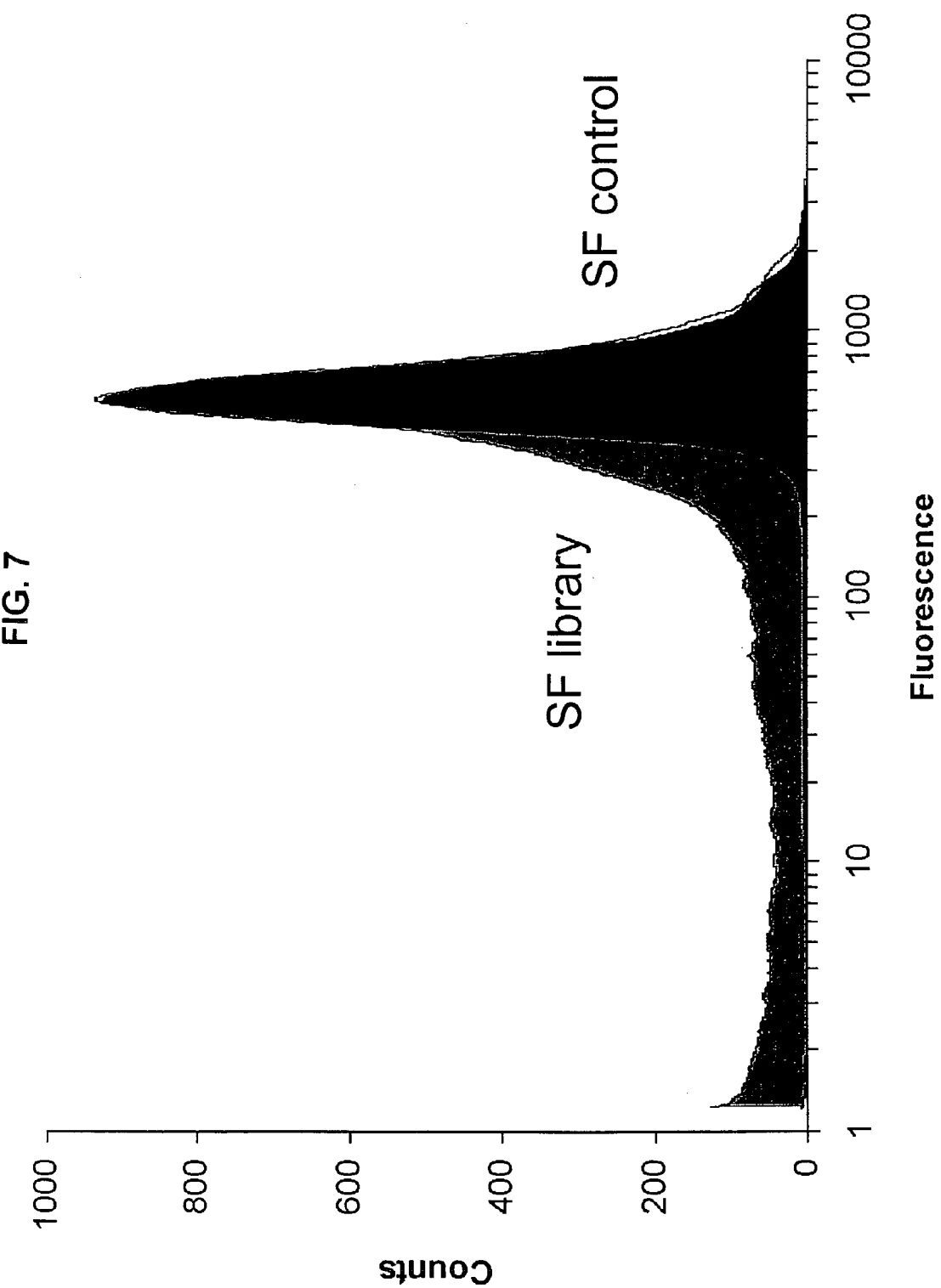

FIG. 7. Flow cytometric analyses of superfolder mutant pool library (grey) or control parental superfolder variant (dark grey). Number of events (cells) y-axis; fluorescence intensity of each event (x-axis). Note the logarithmic fluorescence scale.

Figure 8:
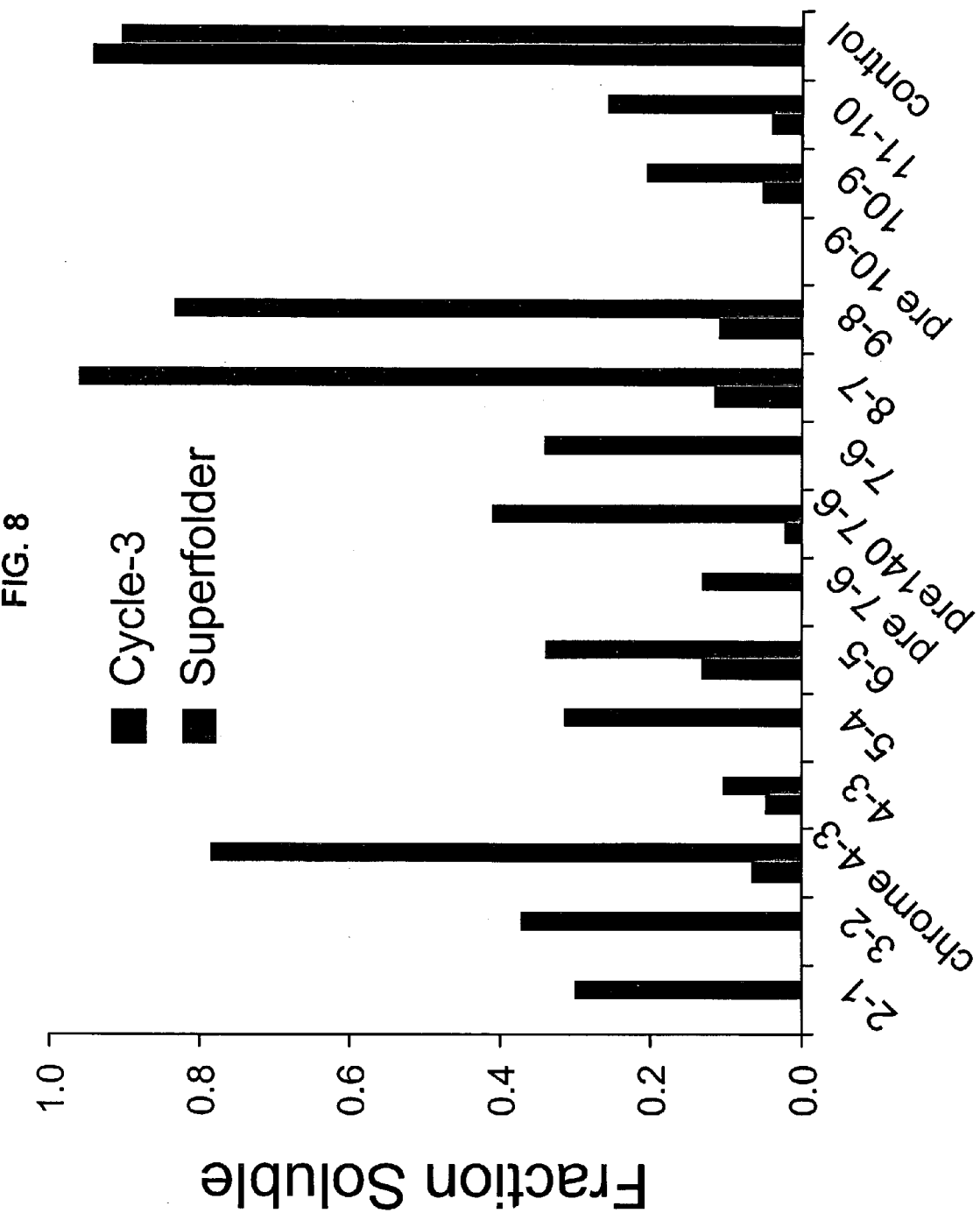

FIG. 8. Solubility of various circular permutants expressed in BL21(DE3) at 37° C. of cycle-3 redshift (black) and superfolder GFP (grey). Normal, non-permutated variants (control). Y-axis, fraction soluble determined by SDS-PAGE densitometry. X-axis, indicated circular permutant (see Table 1 for new starting codon position). As expected, the superfolder is more tolerant to circular permutation (as evidenced by the higher solubility) compared to cycle-3 redshift.

Figure 9:
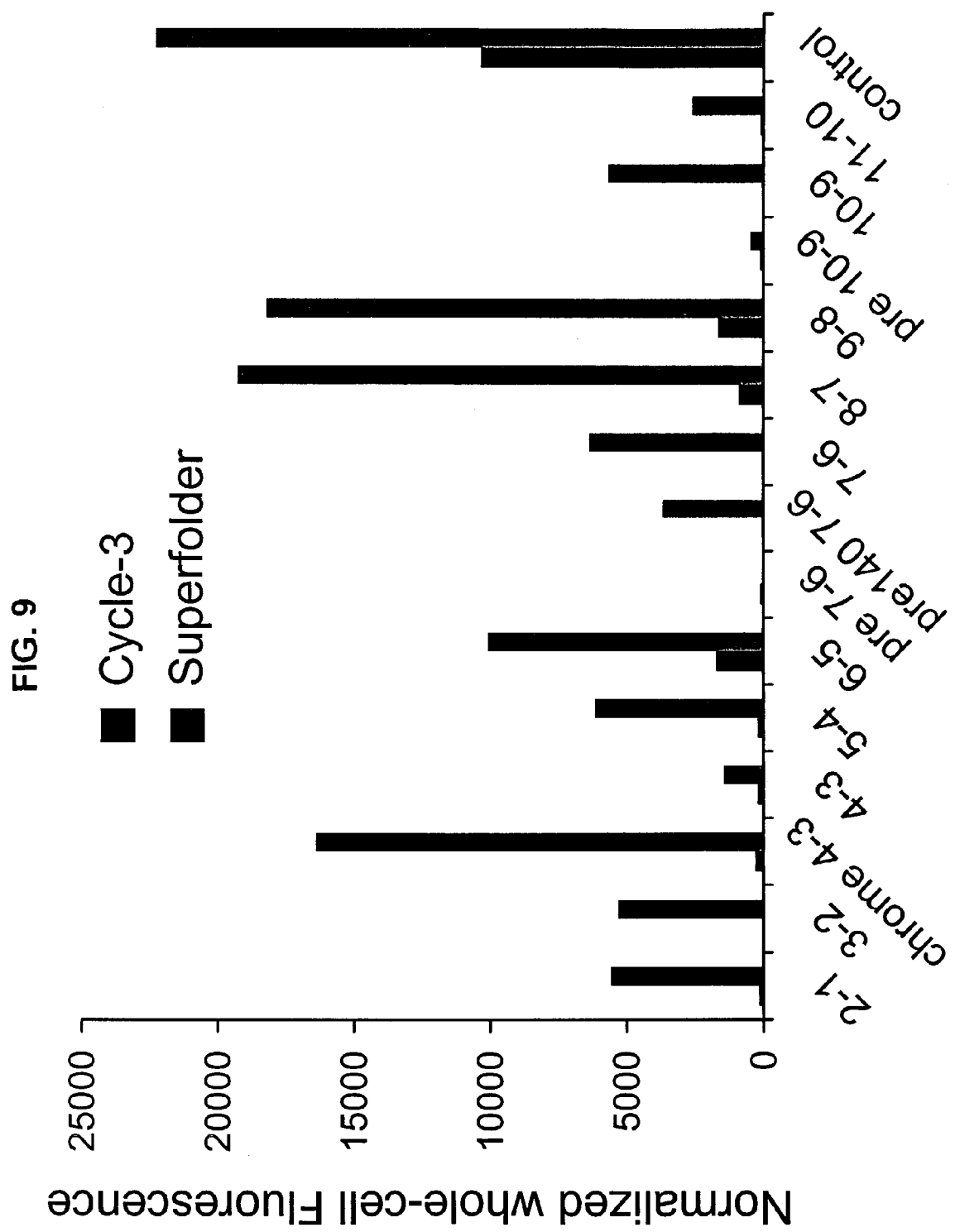

FIG. 9. Whole-cell fluorescence at 37° C. for BL21(DE3) expressing various circular permutants of cycle-3 redshift (black) and superfolder GFP (grey). Fluorescence (488 nm ex/520 nm em) normalized by culture density (absorbance at 600 nm). Normal, non-permutated variants (control). Y-axis, normalized whole cell-fluorescence. X-axis, indicated circular permutant (see Table 1 for new starting codon position). As expected, the superfolder is more tolerant to circular permutation (as evidenced by the higher fluorescence) compared to cycle-3 redshift.

Figure 10:
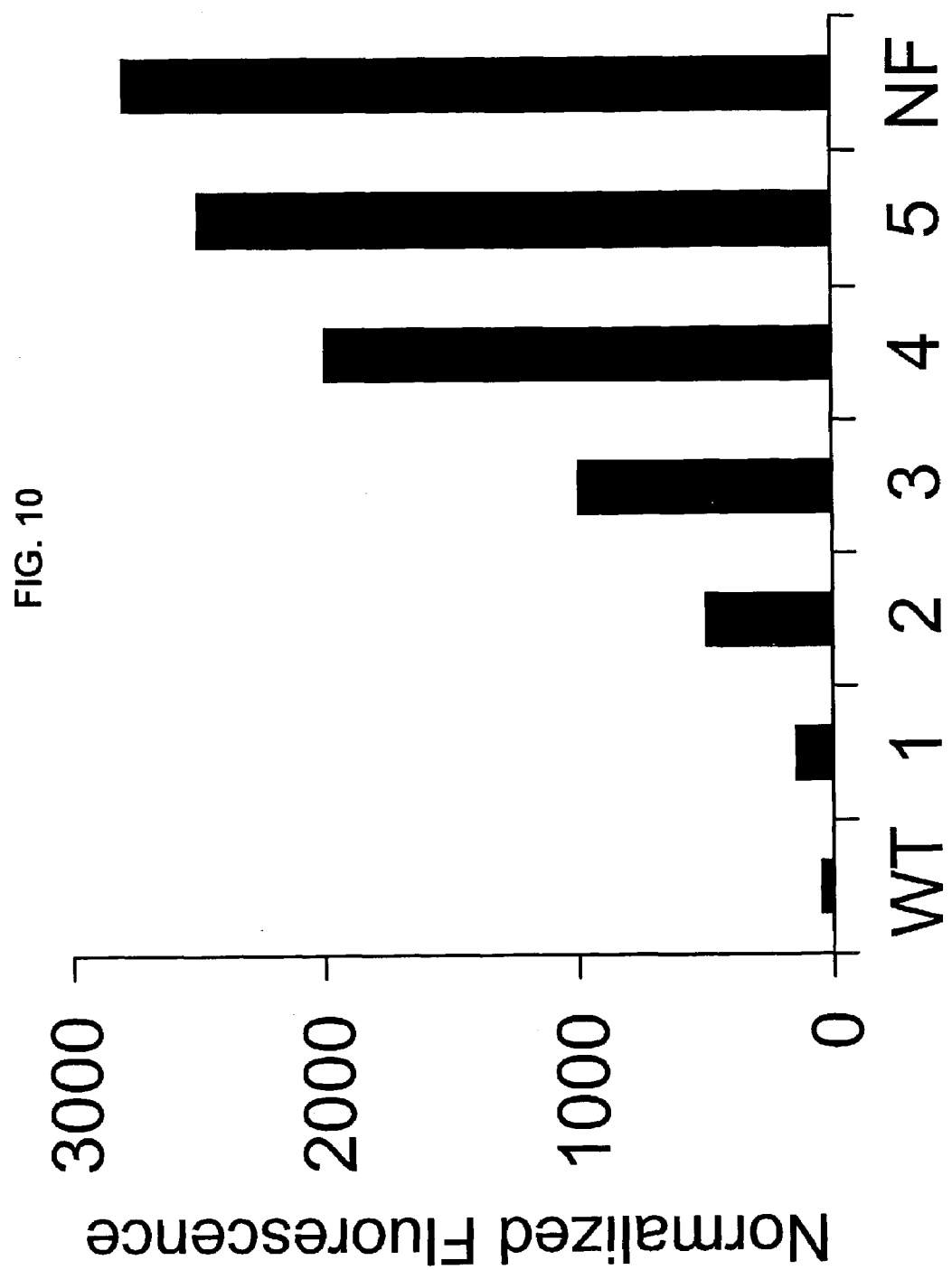

FIG. 10. Whole-cell fluorescence at 37° C. for BL21 (DE3) expressing dsRED variants as C-terminal fusions with poorly-folded bullfrog red-cell H ferritin. Left to right: starting variant (wt); pools of top 10 optima from each round of directed evolution (rounds 1 to 5); non-fusion starting variant (non fusion). Fluorescence (580 nm ex/610 nm em) normalized by culture density (absorbance at 600 nm). As expected, the folding of superfolder dsRED (round 5) is more tolerant to fused upstream misfolded bullfrog red-cell H-ferritin compared to the starting (wt) variant.

DETAILED DESCRIPTION OF THE INVENTION

Introduction

The current invention provides polypeptides with improved folding activity and/or solubility, including superfolding variants of the *Aequorea victoria* Green Fluorescent Protein and Discosoma sp. Red Fluorescent Protein, and methods of obtaining such polypeptides.

Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

A "fluorescent protein" as used herein is a protein that has intrinsic fluorescence. Typically, a fluorescent protein has a structure that includes an 11-stranded beta-barrel.

A "chromophoric protein" or "chromoprotein" are used interchangeably and refer to a class of proteins, recently identified from various corals, a nemones and often sea organisms, which have intrinsic color and, in some cases, variable degrees of intrinsic or inducible fluorescence. Typically, a chromo-protein has a structure similar to the fluorescent proteins, i.e., an 11-stranded beta-barrel.

The "MMDB Id: 5742 structure" as used herein refers to the GFP structure disclosed by Ormo & Remington, MMDB Id: 5742, in the Molecular Modeling Database (MMDB), PDB Id: 1EMA PDB Authors: M. Ormo & S. J. Remington PDB Deposition: 1 Aug. 1996 PDB Class: Fluorescent Protein PDB Title: Green Fluorescent Protein From Aequorea Victoria. The Protein Data Bank (PDB) reference is Id PDB Id: 1EMA PDB Authors: M. Ormo & S. J. Remington PDB Deposition: 1Aug. 1996 PDB Class: Fluorescent Protein PDB Title: Green Fluorescent Protein From *Aequorea Victoria*. (see, e.g., Ormo et al. "Crystal structure of the *Aequorea Victoria* green fluorescent protein." Science Sep. 6, 1996 ;273(5280):1392-5; Yang et al, "The molecular structure of green fluorescent protein." Nat Biotechnol. 1996 October; 14(10):1246-51).

"Root mean square deviation" ("RMSD") refers to the root mean square superposition residual in Angstroms. This number is calculated after optimal superposition of two structures, as the square root of the mean square distances between equivalent C-alpha-atoms.

A "folding interference domain" as used herein refers to a domain that interferes with the folding of a polypeptide ("Xid"). The presence of a folding interference domain in a fusion protein of a polypeptide of interest should detectably interfere with folding, as measured by any criteria capable of discriminating between better and poorer folded versions of the polypeptide of interest, P, within the context of a fusion with Xid. In the practice of the method of the invention, the folding interference domain need not be misfolded itself. In fact, it may not actually be folded at all, and it might be soluble or it might be insoluble. For a folding interference domain, the only requirement is that P in Xid-L-P is delectably less well-folded than P alone ("L" indicates an optional linker polypeptide incorporated between P and Xid in the fusion protein). Further details regarding the detection and assessment of folding is set forth infra.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

"Join" or "link" refers to any method known in the art for functionally connecting protein domains, including without limitation recombinant fusion with or without intervening domains; intein-mediated fusion; non-covalent association; and covalent bonding, including disulfide bonding; hydrogen bonding; electrostatic bonding; and conformational bonding, e.g., antibody-antigen, and biotin-avidin associations.

"Fused" Refers to Linkage by Covalent Bonding.

A "fusion protein" refers to a chimeric molecule formed by the joining of two or more polypeptides through a bond formed one polypeptide and another polypeptide. Fusion proteins may also contain a linker polypeptide in between the constituent polypeptides of the fusion protein. The term "fusion construct" or "fusion protein construct" is generally meant to refer to a polynucleotide encoding a fusion protein.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

A "reporter molecule" has a detectable phenotype. Often, the reporter molecule is a polypeptide, such as an enzyme, or a fluorescent polypeptide. A reporter polypeptide may have intrinsic activity. In the context of the methods of the invention, a reporter molecule has a detectable phenotype associated with correct folding or solubility of the reporter molecule. For example, the reporter could be an enzyme or a fluorescent polypeptide. For an enzyme, the detectable phenotype would then be the ability to turn over a substrate giving a detectable product or change in substrate concentration or physical state. For a fluorescent protein, the activity would be the emission of fluorescence upon excitation by the appropriate wavelength(s) of light.

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., $Nucleic\ Acid\ Res.$ 19:5081 (1991); Ohtsuka et al., $J.\ Biol.\ Chem.$ 260:2605-2608 (1985); Rossolini et al., $Mol.\ Cell.\ Probes$ 8:91-98 (1994)). The term nucleic acid is used interchangeably with gene, cDNA, mRNA, oligonucleotide, and polynucleotide. The terms "polypeptide,""peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "peptidomimetic" and "mimetic" refer to a synthetic chemical compound that has substantially the same structural and functional characteristics of the polypeptides of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, J. $Adv.\ Drug\ Res.$ 15:29 (1986); Veber and Freidinger TINS p. 392 (1985); and Evans et al. $J.\ Med.\ Chem.$ 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of, e.g., —CH2NH—, —CH2S—, —CH2—CH2—, —CH=CH— (cis and trans), —COCH2—, —CH(OH)CH2—, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or fluorescent activities of green fluorescent protein.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Such conservatively modified variants are in addition to and do not exclude polymorphic variants, interspecies homologs, and alleles of the invention.

For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of □-sheet and □-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, 95%, 98% or 99% similar over a specified region or, when not specified, over the entire sequence), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100, 200, 300, 400, 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)). Typically, the Smith & Waterman alignment with the default parameters are used for the purposes of this invention Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. The default parameters of BLAST are also often employed to determined percent identity or percent similarity.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al, *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point (T$_m$) for the specific sequence at a defined ionic strength pH. The T$_m$ is the temperature (under defined ionic strength, pH, and nucleic concentration) at which 50% of the probes complementary to the target hybridize to the target sequence at equilibrium (as the target sequences are present in excess, at T$_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background, hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

An "expression vector" is a nucleic-acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

Directed Evolution Method of Improving Folding and Solubility Characteristics

To improve the folding of a polypeptide, the polypeptide is joined to a folding interference domain, which causes the polypeptide to fold poorly. The DNA encoding the polypeptide can then be mutagenized. Sequence alterations that overcome the poor folding imposed by the folding interference domain can be identified by an increase in the activity of the polypeptide or a reporter linked to the polypeptide. Such sequence mutations can include modification of coding sequence, deletion of coding sequence, insertion of additional coding sequences, change of order of coding sequences, within the existing coding sequence or at the N or C termini (5' or 3' end of the encoding nucleic acid), non-native amino acids. This method was used to generate "superfolder" variants of the Green Fluorescent Protein, GFP, of the luminescent jellyfish Aequorea Victoria and the red fluorescent protein from Discosoma species, DsRed, both of which exhibit enhanced folding and stability properties.

It is often desirable to improve folding of a protein that does not have a detectable activity. For such an application, a detectable moiety can be linked to the target polypeptide/folding interference domain fusion protein to provide a means of assaying for enhanced folding. Thus, the method of selecting robustly-folding proteins has wide applicability.

Where the target protein P has an easily measured phenotype, its folding (or solubility) success can be monitored in the presence of a bait protein domain, herein termed a "folding interference domain" (Xid), as Xid-L-P, for example. These bait domains may also be inserted internally into permissive sites of P, e.g., for GFP at position 145 as further described in the Examples, infra. New variants of target protein P, better suited for folding and/or solubility under stringent conditions can thereby be produced.

When P has no easily measured phenotype associated with correct folding, a reporter domain can be used, for example, in a construct such as Xid-L1-P-L2-R, where R is the reporter domain that tells about the folding of P, Xid is the folding interference domain, and L1 and L2 are flexible linkers.

As will be appreciated by one of skill in the art, this method can also be applied in a block-optimization of a new protein scaffolding, P, comprised of a series of smaller domains, or subdomains of P ($P_1$, $P_2$, etc.). In this embodiment, for example, a construct such as Xid-L-$P_1$-R is used to optimize $P_1$ using R as the reporter. Next, a subdomain, $P_2$, can be added, e.g., in a construct such as Xid-L-$P_2$-$P_1$-R and used to optimize $P_2$ using R as the reporter. Optionally, $P_1$ can be optimized for folding at the same time. The same reporter domain need not be used to optimize each $P_N$. Eventually, after $P_N$ is added, the entire P domain is built from the smaller subdomains.

Thus, the methods of the invention can be used to increase folding and solubility of a target polypeptide as well as subdomains contained within the target polypeptide.

General Nucleic Acid Methodology

The current invention employs basic nucleic acid methodology that is routine in the field of recombinant genetics. Basic texts disclosing the general methods of obtaining and manipulating nucleic acids in this invention include Sambrook and Russell, MOLECULAR CLONING, A LABORATORY MANUAL (3rd ed. 2001) and CURRENT PROTOCOLS IN MOLECULAR BIOLOGY (Ausubel et al., eds., John Wiley & Sons, Inc. 1994-1997, 2001 version)).

Often, the nucleic acid sequences encoding the fusion proteins of the invention are generated using amplification techniques. Examples of techniques sufficient to direct persons of skill through in vitro amplification methods are found in Berger, Sambrook, and Ausubel, as well as Dieffenbach & Dveksler, PCR Primers: A Laboratory Manual (1995): Mullis et al., (1987) U.S. Pat. No. 4,683,202; PCR Protocols A Guide to Methods and Applications (Innis et al., eds) Academic Press Inc. San Diego, Calif. (1990) (Innis); Arnheim & Levinson (Oct. 1, 1990) C&EN 36-47; The Journal Of NIH Research (1991) 3: 81-94; (Kwoh et al. (1989) Proc. Natl. Acad. Sci. USA 86: 1173; Guatelli et al. (1990) Proc. Natl. Acad. Sci. USA 87, 1874; Lomell et al. (1989) J. Clin. Chem., 35: 1826; Landegren et al., (1988) Science 241: 1077-1080; Van Brunt (1990) Biotechnology 8: 291-294; Wu and Wallace (1989) Gene 4:560; and Barringer et al. (1990) Gene 89: 117.

Folding Interference Domains

Folding interference domains can be identified by screening a library. For example, a library can be generated in which peptides fragments are generated to a target protein, e.g., green fluorescent protein, and selecting the recombinants in which the signal from the target protein fused to a peptide fragment is less than, for example, about 10% of the signal from a control recombinant that encodes only the target polypeptide. For example, an assay such as the folding assay disclosed by Waldo et al., in Nature Biotech. 17:691-695, 1999, may be employed. Waldo et al. describe a GFP that does not fold well when fused after bull frog red cell H-ferritin. The folding yield of the GFP in the RanaH-L-GFP fusion was approximately 1/50 that of GFP expressed alone. In that work, several other proteins substantially reduced the folding yield of the GFP domain (<10% that of the GFP alone)

Since the reduction in fluorescence could also be due to a reduction in the level of expression of the fusion protein caused by the trapped peptide fragment, the expression levels of these candidate fusion proteins could subsequently be determined by SDS-PAGE densitometry, for example. Desirable folding interference domains would be those that decrease the folding yield of the test protein or fused reporter domain, while maintaining the level of expression of the fusion protein at a level similar to that of the test protein alone, or the test protein plus reporter domain (i.e., the expression level of the test protein or test protein-reporter domain fusion should be similar to the fusion containing the trapped peptide fragment).

Any number of proteins or protein domains can be used as a folding interference domain. For example, bull frog red cell H-ferritin, folds poorly when expressed by itself, and when included in a fusion polypeptide, causes the fusion polypeptide to fold poorly. Other poorly folding domains include, but are not limited to the Alzheimer's α/β peptide (amino acids 1-40 of the Alzheimer's precursor protein); domain A of the xylR TOL operon regulatory protein of Pseudomonas putida Perez-Martin, J; Cases, I; deLorenzo, V Design of a solubilization pathway for recombinant polypeptides in vivo through processing of a bi-protein with a viral protease PROTEIN ENGINEERING; June 1997; v.10, no.6, p. 725-730; and nucleoside diphosphate kinase of the hyperthermophile Pyrobaculum aerophilum (Pedelacq et al, 2002, Nature Biotechnol. 20 (9): 927-932). Any of the insoluble, poorly folded domains described in Waldo et al., in *Nature Biotech.* 17:691-695, 1999.

The aforementioned folding interference domains are mostly insoluble when expressed alone in *E. coli*. However, the folding interference domain need not be insoluble when expressed alone. Some peptides are at least partially soluble when expressed alone or with well-folded highly soluble polypeptides (~at least 40% soluble), but can nonetheless induce misfolding and poor solubility of many fused polypeptides. Such polypeptides include the lacZα domain (the first 80-100 N-terminal amino acids of the beta galactosidase, a fragment commonly used in protein complementation assays).

The folding interference domain may be linked, either directly or via a linker, to either the N-terminus or C-terminus of the target polypeptide sequence. Alternatively, the domain may be inserted into an internal site of the target polypeptide that is permissive to the insertion. A permissive site of a host protein is one which tolerates the insertion of well-folded, soluble proteins or polypeptides (guest polypeptides) within the host protein scaffolding. Typical sites are turns and sterically open regions. One such example is amino acid residue 87 of *Escherichia coli* dihydrofolate reductase. If the protein has a measurable activity (enzyme, fluorescence, binding ability) associated with the native structure, a site is defined as permissive if the host protein containing the guest polypeptide retains at least 5%, or 10%, or preferably at least 20% of the host protein activity observed without the guest.

Target Polypeptides

A target polypeptide can be any polypeptide for which it is desirable to improve the folding properties. Often such polypeptides include those with reporter activity, such as a fluorescent protein, i.e., green or red fluorescent protein. Other proteins include various enzymes, e.g., antibiotic resistance proteins such as, chloramphenicol acetyltransferase, kanamycin resistance protein, beta-lactamase, tetracycline resistance protein, dihydrofolate reductase; and other enzymes such as subtilisin, fungal xylanases. Other target proteins include antibodies, for which increased binding to the target antigen can be used as the selection criterion.

A particular aspect of the invention relates to the generation of superfolder fluorescent and chromophoric protein variants, and is described in further detail below and in the Examples, infra.

Fluorescent and Chromophoric Proteins

A variety of fluorescent proteins and chromoproteins may be "evolved" according to the methods of the invention to generate variants having improved folding and/or solubility properties. The superfolder fluorescent and chromophoric protein variants generally share a common tertiary structure comprising an 11-stranded beta-barrel structure surrounding a centrally-located self-activating chromophore.

One group of such fluorescent proteins includes the Green Fluorescent Protein isolated from *Aequorea Victoria* (GFP), as well as a number of GFP variants, such as cyan fluorescent protein, blue fluorescent protein, yellow fluorescent protein, etc. Typically, these variants share about 80% or greater sequence identity with the GFP sequence or with SEQ ID NO:2. A number of color shift mutants of GFP have been developed and may be employed in the directed evolution methods of the present invention. These color-shift GFP mutants have emission colors blue to yellow-green, increased brightness, and photostability (Tsien et al., 1998, Annual Review of Biochemistry 67: 509-544). One such GFP mutant, termed the Enhanced Yellow Fluorescent Protein, displays an emission maximum at 529 nm.

Additional GPF-based variants having modified excitation and emission spectra (Tsien et al., U.S. Patent Appn. 20020123113A1), enhanced fluorescence intensity and thermal tolerance (Thastrup et al., U.S. Patent Appn. 20020107362A1; Bjorn et al., U.S. Patent Appn. 20020177189A1), and chromophore formation under reduced oxygen levels (Fisher, U.S. Pat. No. 6,414,119) have also been described. Most recently, GFPs from the anthozoans *Renilla reniformis* and *Renilla kollikeri* were described (Ward et al., U.S. Patent Appn. 20030013849).

Another group of such fluorescent proteins includes the fluorescent proteins isolated from anthozoans, including without limitation the red fluorescent protein isolated from Discosoma species of coral, DsRed (Matz et al., 1999, Nat. Biotechnol. 17:969-973), (see, e.g., accession number AF168419 version AF168419.2). DsRed and the other anthozoan fluorescent proteins share only about 26-30% amino acid sequence identity to the wild-type GFP from *Aequorea Victoria*, yet all the crucial motifs are conserved, indicating the formation of the 11-stranded beta-barrel structure characteristic of GFP.

The crystal structure of DsRed has also been solved, and shows conservation of the 11-stranded beta-barrel structure of GFP MMDB Id: 5742 (Yarbrough et al., 2001, Proc. Natl. Acad. Sci. USA 98: 462-467).

A number of mutants of the longer wavelength red fluorescent protein DsRed have also been described, and similarly, may be employed in the directed evolution methods of the invention. For example, recently described. DsRed mutants with emission spectra shifted further to the red may be employed in the practice of the invention (Wiehleret al., 2001, FEBS Letters 487:384-389; Terskikh et al., 2000, Science 290: 1585-1588; Baird et al., 2000, Proc. Natl. Acad. Sci. USA 97: 11984-11989).

An increasingly large number of other fluorescent proteins from a number of ocean life forms have recently been described, and the Protein Data Bank currently lists a number of GFP and GFP mutant crystal structures, as well as the crystal structures of various GFP analogs. Related fluorescent proteins with similar structures to GFP from corals, sea pens, sea squirts, and sea anemones have been described, and may be used to generate "superfolder" variants (for reviews, see Zimmer, 2002, Chem. Rev. 102: 759-781; Zhang et al., 2002, Nature Reviews 3: 906-918).

Fluorescent proteins from *Anemonia majano*, Zoanthus sp., *Discosoma striata*, Discosoma sp. and Clavularia sp. have also been reported (Matz et al., supra). A fluorescent protein cloned from the stony coral species, *Trachyphyllia geoffroyi*, has been reported to emit green, yellow, and red light, and to convert from green light to red light emission upon exposure to UV light (Ando et al., 2002, Proc. Natl. Acad. Sci. USA 99: 12651-12656). Recently described fluorescent proteins from sea anemones include green and orange fluorescent proteins cloned from *Anemonia sulcata* (Wiedenmann et al., 2000, Proc. Natl. Acad. Sci. USA 97: 14091-14096), a naturally enhanced green fluorescent protein cloned from the tentacles of *Heteractis magnifica* (Hongbin et al., 2003, Biochem. Biophys. Res. Commun. 301: 879-885), and a generally non fluorescent purple chromoprotein displaying weak red fluorescence cloned from *Anemonia sulcata*, and a mutant thereof displaying far-red shift emission spectra (595 nm) (Lukyanov et al., 2000, J. Biol. Chem. 275: 25879-25882).

Additionally, another class of GFP-related proteins having chromophoric and fluorescent properties have been described. One such group of coral-derived proteins, the pocilloporins, exhibit a broad range of spectral and fluorescent characteristics (Dove and Hoegh-Guldberg, 1999, PCT application WO 00/46233; Dove et al., 2001, Coral Reefs 19: 197-204). Recently, the purification and crystallization of the pocilloporin Rtms5 from the reef-building coral *Montipora efflorescens* has been described (Beddoe et al., 2003, Acta Cryst. D59: 597-599). Rtms5 is deep blue in color, yet is weakly fluorescent. However, it has been reported that Rtms5, as well as other chromoproteins with sequence homology to Rtms5, can be interconverted to a far-red fluorescent protein via single amino acid substitutions (Beddoe et al., 2003, supra; Bulina et al., 2002, BMC Biochem. 3:7; Lukyanov et al., 2000, supra).

Various other coral-derived chromoproteins closely related to the pocilloporins are also known (see, for example,-Lukyanov et al. 2000, J. Biol. Chem. 275: 25879-82; Gurskaya et al., 2001, FEBS Letters 507: 16-20).

In one embodiment, fluorescent and chromophoric protein variants exhibiting enhanced folding or solubility are generated from any fluorescent or chromophoric protein having a structure with a root mean square deviation of less than 5 angstroms, often less than 3, or 4 angstroms, and preferably less than 2 angstroms from the 11-stranded beta-barrel structure of *Aequorea victoria* GFP MMDB Id:5742. In some cases, fluorescent proteins exist in multimeric form. For example, DsRed is tetrameric (Cotlet et al., 2001, Proc. Natl. Acad. Sci. USA 98: 14398014403). As will be appreciated by those skilled in the art, structural deviation between such multimeric fluorescent proteins and GFP (a monomer) is evaluated on the basis of the monomeric unit of the structure of the fluorescent protein.

As appreciated by one of ordinary skill in the art, such a suitable fluorescent protein or chromoprotein structure can be identified using comparison methodology well known in the art. In identifying the protein, a crucial feature in the alignment and comparison to the MMDB ID:5742 structure is the conservation of the 11 beta strands, and the topology or connection order of the secondary structural elements (see, e.g., Ormo et al. "Crystal structure of the *Aequorea victoria* green fluorescent protein." Yang et al, 1996, Science273: 5280,1392-5; Yang et al., 1996 *Nat Biotechnol.* 10:1246-51). Typically, most of the deviations between a fluorescent protein and the GFP structure are in the length(s) of the connecting strands or linkers between the crucial beta strands, see, e.g., the comparison of DsRed and GFP (Yarbrough et al. , 2001,. Proc Natl Acad Sci USA 98:462-7). In Yarbrough et al., alignment of GFP and DsRed is shown pictorially. From the stereo diagram, it is apparent that the 11 beta-strand barrel is rigorously conserved between the two structures. The c-alpha backbones are aligned to within 1 angstrom RMSD over 169 amino acids although the sequence identity is only 23% comparing DsRed and GFP.

In comparing structure, the two structures to be compared are aligned using algorithms familiar to those with average skill in the art, using for example the CCP4 program suite. COLLABORATIVE COMPUTATIONAL PROJECT, NUMBER 4. 1994. "The CCP4 Suite: Programs for Protein Crystallography". Acta Cryst. D50, 760-763. In using such a program, the user inputs the PDB coordinate files of the two structures to be aligned, and the program generates output coordinates of the atoms of the aligned structures using a rigid body transformation (rotation and translation) to minimize the global differences in position of the atoms in the two structures. The output aligned coordinates for each structure can be visualized separately or as a superposition by readily-available molecular graphics programs such as RASMOL, Roger A. Sayle and E. J. Milner-White, "RasMol: Biomolecular graphics for all", Trends in Biochemical Science (TIBS), September 1995, Vol. 20, No. 9, p. 374.), or Swiss PDB Viewer, Guex, N and Peitsch, M.C.(1996) Swiss-PdbViewer: A Fast and Easy-to-use PDB Viewer for Macintosh and PC. Protein Data Bank Quarterly Newsletter 77, pp. 7.

In considering the RMSD, the RMSD value scales with the extent of the structural alignments and this size is taken into consideration when using the RMSD as a descriptor of overall structural similarity. The issue of scaling of RMSD is typically dealt with by including blocks of amino acids that are aligned within a certain threshold. The longer the unbroken block of aligned sequence that satisfies a specified criterion, the 'better' aligned the structures are. In the DsRed example, 164 of the c-alpha carbons can be aligned to within 1 angstrom of the GFP. Typically, users skilled in the art will select a program that can align the two trial structures based on rigid body transformations, for example DALI, Holm, L. & Sander, C. Protein-structure comparison by alignment of distance matrices. *Journal of Molecular Biology* 1993, 233, 123-138. The server site for the computer implementation of the algorithm is available, for example, at dali@ebi.ac.uk. The output of the DALI algorithm are blocks of sequence that can be superimposed between two structures using rigid body transformations. Regions with Z-scores at or above a threshold of Z=2 are reported as similar. For each such block, the overall RMSD is reported.

GFP Proteins with Improved Folding Activity

Superfolding GFP proteins were generated using the methods set forth herein. These proteins exhibit increased folding compared to wild type GFP or the "Crameri" cycle 3 GFP (GFP3) (Crameri et al., *Eur. J. Biochem.* 226:53-58, 1994).

The improved GFPs of the invention comprise at least 80% identity to SEQ ID NO: 5 and contain at least one amino acid substitution selected from the group consisting of a substitution at position 30 that is an arginine or a conservative variant of arginine; a substitution at position 39 that is an asparagine or a conservative variant of asparagine; a substitution at position 105 that is a threonine or a conservative variant of threonine; a substitution at position 171 that is a valine or a conservative variant of valine; and a substitution at position 206 that is a valine or a conservative variant of valine.

In a particular embodiment, a superfolder GFP variant ("GFP$_{SF}$") containing the foregoing five amino acid substitutions on a GFP3 background is provided.

The positions are typically determined with reference to SEQ ID NO: 5. Thus, as appreciated by one of skill in the art, the positions do not refer to the number of amino acids in the protein, but the position relative to SEQ ID NO: 5. For example, a GFP sequence is maximally aligned with SEQ ID NO: 5, for example by manual alignment or using the Smith & Waterman alignment (see, e.g., *Adv. Appl. Math.* 2:482 (1981)) with the default parameters. The residue of the GFP sequence that aligns with position 30 of SEQ ID NO: 5, is considered to be position 30 of the GFP sequence.

The presence of the substitution at the position of the protein results in improved folding of the green fluorescent protein.

A "green" fluorescent protein of the invention often fluoresces green, but may also have yellow or blue fluorescence. For example, a single amino acid change provide detail shifts the fluorescence from green to blue. A superfolding yellow fluorescent protein (sfYFP) can be made from the superfolding GFP disclosed herein by adding the single amino acid change T203Y. Alternatively, folding of the existing BFP and YFP proteins (Tsien, 1998) Annu. Rev. Biochem. 67: 509-544; Miyawaki et al,1999, Proc. Natl. Acad. Sci. USA 96: 2135-2140), which is equivalent to the canonical GFP with the mutations S65G, V68L, Q69K, 72A, and T203Y). can each also be improved by making the substitutions disclosed herein.

DsRed Fluorescent Proteins With Enhanced Folding

The directed evolution method of the invention has also applied to the generation of a superfolder DsRed fluorescent protein. In a particular embodiment, a superfolder DsRed variant ("DsRed$_{SF}$") is provided, and has the amino acid sequence of SEQ ID NO: 4 One example of a polynucleotide encoding DsRed$_{SF}$ has the nucleotide sequence of SEQ ID NO: 3

Generation of the Fusion Protein

Typically an amino acid linker sequence is employed to separate the first and second polypeptide components by a distance sufficient to ensure that each polypeptide could fold into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that can interact with functional epitopes on the firsthand second polypeptides; and (3) the lack of hydrophobic or charged residues that might react with the polypeptide functional epitopes. Typical peptide linker sequences contain Gly, Ser, Ala, Val and Thr residues. Often, a linker is a "flexible linker", that has a sequence such as $(Gly_4Ser)_x$, e.g., $(Gly_4Ser)_3$.

Amino acid sequences which may be usefully employed as linkers include those disclosed in Maratea et al (1985) Gene 40:39-46; Murphy et al. (1986) Proc. Natl. Acad. Sci. USA 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences may not be required when the first and second polypeptides have non-essential N-terminal amino acid regions that can be used to separate the functional domains and prevent steric interference.

Other methods of joining the components of the chimeric protein include ionic binding by expressing negative and positive tails, and indirect binding through antibodies and streptavidin-biotin interactions. (See, e.g., *Bioconjugate Techniques*, supra). The components can also be joined together through an intermediate interacting sequence. The moieties included in the conjugate molecules can be joined in any order, although the most favorable configuration may be determined empirically.

Production of Proteins Using Recombinant Techniques

Well known recombinant methodology is used to generate the fusion proteins used in the practice of the method of the invention. Fusion constructs can be made by ligating the appropriate nucleic acid sequences encoding the desired amino acid sequences to each other by methods known in the art, in the proper reading frame, and expressing the product by methods known in the art. Nucleic acids encoding the domains to be incorporated into the fusion proteins of the invention can be obtained using routine techniques in the field of recombinant genetics (see, e.g., Sambrook and Russell, eds, *Molecular Cloning: A Laboratory Manual*, 3rd Ed, vols. 1-3, Cold Spring Harbor Laboratory Press, 2001; and *Current Protocols in Molecular Biology*, Ausubel, ed. John Wiley & Sons, Inc. New York, 1997).

Often, the nucleic acid sequences encoding the component domains to be incorporated into the fusion protein are cloned from cDNA and genomic DNA libraries by hybridization with probes, or isolated using amplification techniques with oligonucleotide primers. Amplification techniques can be used to amplify and isolate sequences from DNA or RNA (see, e.g., Dieffenbach & Dveksler, PCR Primers: A Laboratory Manual (1995)). Alternatively, overlapping oligonucleotides can be produced synthetically and joined to produce one or more of the domains. Nucleic acids encoding the component domains can also be isolated from expression libraries using antibodies as probes.

In an example of obtaining a nucleic acid encoding a domain to be included in the conjugate molecule using PCR, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be easily ligated into a vector containing a nucleic acid encoding the second domain and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

In some embodiments, it may be desirable to modify the polypeptides encoding the components of the conjugate molecules. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81-97, Roberts et al. (1987) *Nature* 328: 731-734.

For example, the domains can be modified to facilitate the linkage of the two domains to obtain the polynucleotides that encode the fusion polypeptides of the invention. Catalytic domains and binding domains that are modified by such methods are also part of the invention. For example, a codon for a cysteine residue can be placed at either end of a domain so that the domain can be linked by, for example, a disulfide linkage. The modification can be performed using either recombinant or chemical methods (see, e.g., Pierce Chemical Co. catalog, Rockford Ill.).

The domains of the recombinant fusion proteins are often joined by linkers, usually polypeptide sequences of neutral amino acids such as serine or glycine, that can be of varying lengths, for example, about 200 amino acids or more in length, with 1 to 100 amino acids being typical. Often, the linkers are 10, 15, 20, 25, 30, 35, 40, 45, or 50 amino acid residues or less in length. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art. Typically, a flexible linker is a peptide linker of any length whose amino acid composition is rich in glycine to minimize the formation of rigid structure by interaction of amino acid side chains with each other or with the polypeptide backbone. A typical flexible linker has the composition $(Gly_4Ser)_x$.

In some embodiments, the recombinant nucleic acids encoding the fusion proteins of the invention are modified to provide preferred codons which enhance translation of the nucleic acid in a selected organism (e.g., yeast preferred codons are substituted into a coding nucleic acid for expression in yeast).

Mutagenesis

Target polypeptides with enhanced folding ability are typically identified by mutating the nucleic acid sequence encoding the target polypeptide, generating a fusion protein (comprising the mutated target polypeptide, a poorly folding domain, and optionally, a reporter gene), and selecting those polypeptides with enhanced reporter activity, thus identifying target polypeptides that overcome the poor folding property imposed by the poorly folding domain.

The nucleic acid sequences encoding the target polypeptide of interest can be mutated using methods well known to those of ordinary skill in the art. The target polypeptide is usually mutated by mutating the nucleic acid. Techniques for mutagenizing are well known in the art. These include, but are not limited to, such techniques as error-prone PCR, chemical mutagenesis, and cassette mutagenesis Alternatively, mutator strains of host cells may be employed to add mutational frequency (Greener and Callahan (1995) *Strategies in Mol. Biol.* 7: 32). For example, error-prone PCR (see, e.g., Ausubel, supra) uses low-fidelity polymerization conditions to introduce a low level of point mutations randomly over a long sequence. Other mutagenesis methods include, for example, recombination (WO98/42727); oligonucleotide-directed mutagenesis (see, e.g., the review in Smith, *Ann. Rev.Genet.* 19: 423-462 (1985); Botstein and Shortle, *Science* 229: 1193-1201 (1985); Carter, *Biochem. J.* 237: 1-7 (1986); Kunkel, "The efficiency of oligonucleotide directed mutagenesis" in Nucleic acids & Molecular Biology, Eckstein and Lilley, eds., Springer Verlag, Berlin (1987), *Methods in Enzymol.* 100: 468-500 (1983), and *Methods in Enzymol.* 154: 329-350 (1987)); phosphothioate-modified DNA mutagenesis (Taylor et al., *Nucl. Acids Res.* 13: 8749-8764 (1985); Taylor et al., *Nucl. Acids Res.* 13: 8765-8787 (1985); Nakamaye and Eckstein, *Nucl. Acids Res.* 14: 9679-9698 (1986); Sayers et al., *Nucl. Acids Res.* 16:791-802 (1988); Sayers et al., *Nucl Acids Res.* 16: 803-814 (1988)), mutagenesis using uracil-containing templates (Kunkel, *Proc. Nat'l. Acad. Sci. USA* 82: 488-492 (1985) and Kunkel et al, Methods in Enzymol. 154:367-382, 1987); mutagenesis using gapped duplex DNA (Kramer et al., *Nucl. Acids Res.* 12: 9441-9456 (1984); Kramer and Fritz, *Methods in Enzymol.* 154:350-367 (1987); Kramer et al., *Nucl. Acids Res.* 16: 7207 (1988)); and Fritz et al., *Nucl. Acids Res.* 16: 6987-6999 (1988)). Additional methods include point mismatch repair (Kramer et al, *Cell* 38: 879-887 (1984)), mutagenesis using repair-deficient host strains (Carter et al., *Nucl. Acids Res.* 13: 4431-4443 (1985); Carter, *Methods in Enzymol.* 154: 382-403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond.* A 317: 415-423 (1986)), mutagenesis by total gene synthesis (Nambiar et al., *Science* 223: 1299-1301 (1984); Sakamar and Khorana, *Nucl. Acids Res.* 14: 6361-6372 (1988); Wells et al., *Gene* 34:315-323 (1985); and Grundstrom et al., *Nucl. Acids Res.* 13: 3305-3316 (1985). Kits for mutagenesis are commercially available (e.g., Bio-Rad, Amersham International). More recent approaches include codon-based mutagenesis, in which entire codons are replaced, thereby increasing the diversity of mutants generated,- as exemplified by the RID method described in Murakami et al., 2002, Nature Biotechnology, 20: 76-81.

Folding Detection and Assessment

Folding may be detected and assessed using various tests commonly used to determine correct folding, including without limitation spectroscopy, resistance to denaturation, kinetics, and tolerance for additional random mutations and polypeptide insertions. In one embodiment, circular dichroism may be used to distinguish between folded and unfolded forms of a polypeptide. In another embodiment, folding kinetics may be used, wherein better folded versions of P are identified by their ability to adopt a correctly folded conformation faster than poorer folding variants or the wild type protein. Preferably, the evolved polypeptide will display about a 25% faster refolding time following denaturation.

In another embodiment, resistance to denaturation may be used to assess folding. For example, increasing concentrations of urea may be used to assess more robustly folding variants. A polypeptide variant with significantly improved folding activity is typically one which can tolerate about a 0.5 molar higher urea concentration compared to the wild type or starting polypeptide.

Tolerance to random mutations may also be used to assess the folding enhancement achieved following polypeptide evolution. Briefly, a library of random mutants of both the wild type (or pre-evolved) polypeptide and the test evolved polypeptide are generated. A 0.7% amino acid mutation rate, for example, may be appropriate. The library clones are then evaluated for fluorescence as a measure of correct folding. The presence and extent to which the evolved polypeptide mutant library displays a greater number of fluorescent clones relative to the wild type mutant library indicates the folding robustness of the evolved test polypeptide.

Similarly, tolerance to terminally fused or inserted polypeptides may provide an indication of the folding enhancement achieved following the directed evolution method of the invention. In one embodiment, random insertion mutant libraries may be created using, for example, transposon-mediated mutagenesis techniques (Gorshin et al., 2000, Nature Biotechnol. 18: 97) and commercially available kits (e.g., Epicentre Technologies, Madison, Wis.). More robustly folding mutants in the evolved mutant library relative to the unevolved mutant polypeptide library provides an indication of the extent to which the evolved test polypeptide has enhanced folding properties. Similarly, the tolerance to larger insertions may provide an indication of the extent to which the evolved polypeptide has acquired enhanced folding properties.

Another method for evaluating acquisition of enhanced folding in evolved polypeptides involves the generation of circular permutants of the test evolved polypeptide. Briefly, the native N and C termini of the test evolved polypeptide are ligated together at the polynucleotide level, and start codons are randomly introduced into the coding sequence. A library of circular permutants is then expressed and compared to a library of circular permutants generated from the unevolved polypeptide, wherein the relative number of permissive sites for the randomly inserted start codons may be determined by a functional screen indicative of correct folding and thereby provides an indication of folding enhancement acquired by the evolved polypeptide.

In general, superfolder polypeptides will enable the generation of a greater range of circular permutants, relative to the wild type or pre-evolved polypeptide from which the superfolder was generated. This is a particularly important consideration in regards to fluorescent proteins, for which the generation of a variety of circular permutants is desirable for developing appropriate FRET pairs. FRET, or Fluorescence Resonance Energy Transfer, is the non-radiative transfer of energy from a donor fluorophore to an acceptor fluorophore spatially located within about 80 Angstroms of each other. The relative geometric context of the two fluorophores is an important component of FRET. Circular permutation may be used to alter the geometric orientation of the fluorophores relative to each other.

Functional assays may also be utilized where appropriate, and may be preferred. For example, a biological property of a protein of interest may be measured as an indication of folding. For example, if the protein is a fluorescent or chromophoric protein, the presence and intensity of emitted fluorescence or color, respectively, provides an indication of folding. Brighter fluorescence, for example, provides an indication of better folding in relation to dimmer variants of P (or colonies expressing P).

Additionally, misfolded proteins often aggregate and become insoluble, and a corresponding test may be applied by first determining that the correctly folded protein is soluble, and that the incorrectly folded protein is insoluble. For example, if the protein is an enzyme, and the correctly folded enzyme is active and its activity can be measured, and the soluble protein is, active while the insoluble protein is inactive, then if Xid-L-P is soluble and active, P would be inferred to be correctly folded. If Xid-L-P is not active, and also insoluble, then it may be concluded that P is misfolded. Xid-L-P might be active and yet insoluble, or Xid-L-P might be soluble but inactive.

Alternatively, the solubility of Xid-L-P could be used to determine the folding of P in Xid-L-P as above. If the correctly folded version of P binds a target peptide Pt, and the binding can be detected, for example if Pt is an antibody that is conjugated to a reporter domain R, or has and intrinsically detectable signal, or P and Pt are binding or folding partners, or P and Pt comprise two of at least two domains of a split protein or multiprotein complex, which has a detectable phenotype when the fragments or components are assembled, the assembly dependent on the correct folding of P in Xid-L-P. Also, folding of P could be measured by the resistance of P to limited proteolysis coupled to selection by phage display (in which case the method is a way of increasing the stringency of selection by phage display (Martin et al., 2001, J. Mol. Biol. 309(3): 717-26.

Also, the folding of P in Xid-L-P could be detected by using a folding reporter such as GFP or some other protein with a detectable phenotype (enzyme activity, fluorescence, ability to bind other proteins or molecules) such that the detection of R in Xid-L-P-R is an indication of correct folding by R and therefore of P (see Waldo patent "method for determining and modifying protein/peptide solubility").

Detectable phenotypes are not limited to enzymatic activity or fluorescence. For example, the phenotype associated with correct folding of P could be the ability of P to bind a target molecule, the binding event being detectable by some means. In this case, the reporter domain might not have activity until the binding event occurs. For example, P could be a component of a complementation system or split protein such as the S-protein or S-peptide (which associate to form active RNASE-A), or the split dihydrofolate reductase, or the split beta lactamase (Galarneau, A; Primeau, M; Trudeau, L E; Michnick, S W Beta-lactamase protein fragment complementation assays as in vivo and in vitro sensors of protein-protein interactions Nature Biotechnology; June 2002; v.20, no.6, p. 619-622, or the split beta galactosidase (Wigley, W C; Stidham, R D; Smith, N M; Hunt, J F; Thomas, P J Protein solubility and folding monitored in vivo by structural complementation of a genetic marker protein Nature Biotechnology; February 2001; v.19, no.2, p. 131-136). The split proteins could be self-assembling, or require the association via fused partners that are capable of association, such as coiled-coils. (Galarneau, A; Primeau, M; Trudeau, L E; Michnick, SW Beta-lactamase protein fragment-complementation assays as in vivo and in vitro sensors of protein-protein interactions Nature Biotechnology; June 2002; v.20, no.6, p. 619-622.

It is desirable that the signal level given as the detectable phenotype be proportionate to the amount of correctly folded reporter molecule. The binding event could be that of an antibody that recognizes an epitope of the correctly-folded target P, binding of the antibody measured by some means such as the enzymatic activity of a linked enzyme.

The mutated target polypeptides tested for folding activity in the context of a fusion protein comprising a poorly folding domain, which was selected for its poor folding properties in the expression system of interest. Folding activity is typically measured by measuring the amount of reporter activity, as the amount of active protein is dependent on proper folding. The target polypeptide may itself have reporter activity or may be joined to another molecule that has reporter activity.

Reporter molecules that can be used include those with activities that can be directly measured, e.g., fluorescent polypeptides, e.g., green, blue, yellow, or red fluorescent proteins and variants of those proteins; polypeptides encoded by antibiotic resistance genes; and molecules that can be indirectly measured, e.g., enzymes such as β-galactosidase, alkaline phosphatase, horse radish peroxidase, β-lactamase, or other enzymes that require a secondary detection reagent. Other polypeptides such as antibodies or other binding protein, may be measured by assessing their ability to specifically bind to a binding partner. Other polypeptides could be parts of 'split protein' complementing pairs. Such as DHFR (1-105) and DHFR (106-186) from murine dihydrofolate reductase (see, Remy et al., 1999, Proc. Natl. Acad. Sci. USA, 96: 5394-5399). Also, various split proteins such as beta lactamase, beta galactosidase, etc. Also, this assay can be performed in vitro using cell free-expression and appropriate substrates (fluorogenic, chemoluminescent, etc.; see Galacton Star reagent for beta galactosidase, a ribonucleic acid donor/quencher substrate which is the target of RNASE-A, for example, the split S-protein S-peptide system (Novagen) Kelemen, B R; Klink, T A; Behlke, M A; Eubanks, S R; Leland, P A; Raines, R T Hypersensitive substrate for ribonucleases Nucleic Acids Research; Sep. 15, 1999; v.27, no.18, p. 3696-3701.

Various non-polypeptide reporters may also be employed, such as cyclic arseno compounds capable of binding to poly cysteine tags on proteins and cyclizing to become fluorescent. (Adams et al., 2002, Journal Of The American Chemical Society, 124: 6063-6076). Polypeptide with enhanced folding properties are then selected and can be obtained in the quantity desired using various expression systems.

Expression Cassettes and Host Cells for Expressinq Polypeptides

There are many expression systems for producing the proteins of the invention, e.g., the GFP variants with enhanced folding or the fusion proteins, that are well know to those of ordinary skill in the art. (See, e.g., *Gene Expression Systems*, Fernandes and Hoeffler, Eds. Academic Press, 1999; Ausubel, supra; Russell & Sambrook, supra.) The protein may be, but need not be, expressed in the system in which the folding properties were determined. The polynucleotide that encodes the fusion polypeptide is placed under the control of a promoter that is functional in the desired host cell. An extremely wide variety of promoters are available, and can be used in the expression vectors of the invention, depending on the particular application. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (De-Boer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used. Standard bacterial expression vectors include plasmids such as pBR322-based plasmids, e.g., pBLUESCRIPT™, pSKF, pET23D, λ-phage derived vectors, p15A-based vectors (Rose, *Nucleic Acids Res.* (1988) 16:355 and 356) and fusion expression systems such as GST. Epitope tags can also be added to recombinant proteins to provide convenient methods of isolation, e.g., c-myc, HA-tag, 6-His tag, maltose binding protein, VSV-G tag, anti-DYKDDDDK tag, or any such tag, a large number of which are well known to those of skill in the art.

For expression of fusion polypeptides in prokaryotic cells other than *E. coli*, regulatory sequences for transcription and translation that function in the particular prokaryotic species is required. Such promoters can be obtained from genes that have been cloned from the species, or heterologous promoters can be used. For example, the hybrid trp-lac promoter functions in *Bacillus* in addition to *E. coli*. These and other suitable bacterial promoters are well known in the art and are described, e.g., in Russell & Sambrook and Ausubel et al. Bacterial expression systems for expressing the proteins of the invention are available in, e.g., *E. coli, Bacillus sp.*, and *Salmonella* (Palva et al., *Gene* 22:229-235 (1983); Mosbach et al., *Nature* 302:543-545 (1983). Kits for such expression systems are commercially available.

Similarly, the for expression of fusion polypeptides in eukaryotic cells, transcription and translation sequences that function in the particular eukaryotic species are required. For example, eukaryotic expression systems for mammalian cells, yeast, and insect cells are well known in the art and are also commercially available. In yeast, vectors include Yeast Integrating plasmids (e.g., Ylp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include those employing the CMV promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; T abor et al. (1985) *Proc. Nat'l. Acad. Sci. USA* 82: 1074-8). These promoters and their use are discussed in Sambrook et al., supra.

Inducible promoters for other organisms are also well known to those of skill in the art. These include, for example, the metallothionein promoter, the heat shock promoter, as well as many others.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The construction of polynucleotide constructs generally requires the use of vectors able to replicate in host bacterial cells, or able to integrate into the genome of host bacterial cells. Such vectors are commonly used in the art. A plethora of kits are commercially available for the purification of plasmids from bacteria (for example, EasyPrepJ, FlexiPrepJ, from Pharmacia Biotech; StrataCleanJ, from Stratagene; and, QIAexpress Expression System, Qiagen). The isolated and purified plasmids can then be further manipulated to produce other plasmids, and used to transform cells.

The polypeptides can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., *Bio/Technology* (1984) 2: 800; Schoner et al., *Bio/Technology* (1985) 3: 151). Fusion polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the recombinant fusion polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 90 to 95% homogeneity are preferred, and 98 to 99% or more homogeneity are most preferred.

To facilitate purification of the fusion polypeptides of the invention, the nucleic acids that encode the fusion polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells).

Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

Uses of Evolved Polypeptides with Improved Folding Properties

Evolved polypeptides with improved folding can be used in any number of applications. In particular, those target polypeptides that can be used as reporter proteins can be used to report expression level, unaffected by folding. Conventional methods for assessing protein expression in vivo, require poorly folded proteins to be unfolded, for example, prior to probing with labeled antibodies. These proteins do not generally refold well prior to probing or sandwich ELISA, leading to an underestimate of expression level as the misfolded aggregated protein domains are not available for binding by the antibody. Obviously this denaturing method is not suited for intact, high throughput in vivo protein expression monitoring. Furthermore, conventional methods for assessing protein expression in vivo do not work well when the protein domains are buried in aggregates. In contrast, the reporter activity of a polypeptide that has enhanced folding can more accurately reflect expression.

In particular, the GFP and DsRed variants described herein that have improved folding activity can be used in many in vivo and high throughput applications. For example, Xid-L-GFP$_{SF}$ fluorescence is a direct indicator of total expression levels. The assay can thus be applied to single cells using flow cytometry.

Furthermore, the superfolder fluorescent proteins provided herein provide new and more stable scaffolds for the creation of new GFP variants based on circular permutation.

Various aspects of the invention are further described and illustrated by way of the several examples which follow, none of which are intended to limit the scope of the invention.

EXAMPLES

Example 1

The following example describes the use of the method of the invention to generate superfolding variants of GFP.

To create the 'superfolder' GFP variant, a 'directed evolution' experiment was performed in which a poorly folded ferritin domain was linked to the sequence of a GFP3 domain (Crameri variant plus F64L and S65T)(Waldo et al., 1999, Nature Biotechnol. 17: 691-695. The ferritin domain provided the 'bait' to challenge the GFP3 to fold under stringent conditions.

After three rounds of in vitro mutation and recombination, followed by in vivo selection, there was no further increase in the brightness of the colonies. Twelve clones were selected and sequenced by fluorescent dye dideoxy-terminator sequencing technology. Most of the clones contained at least 5 of 6 consensus mutations. The consensus mutations were S30R, Y39N, N105T, Y145F, I171V, and A206V. The resulting GFP, termed superfolder GFP (GFP$_{SF}$), was many-fold brighter as a fusion with ferritin compared to the starting GFP3 variant.

Figure 1:
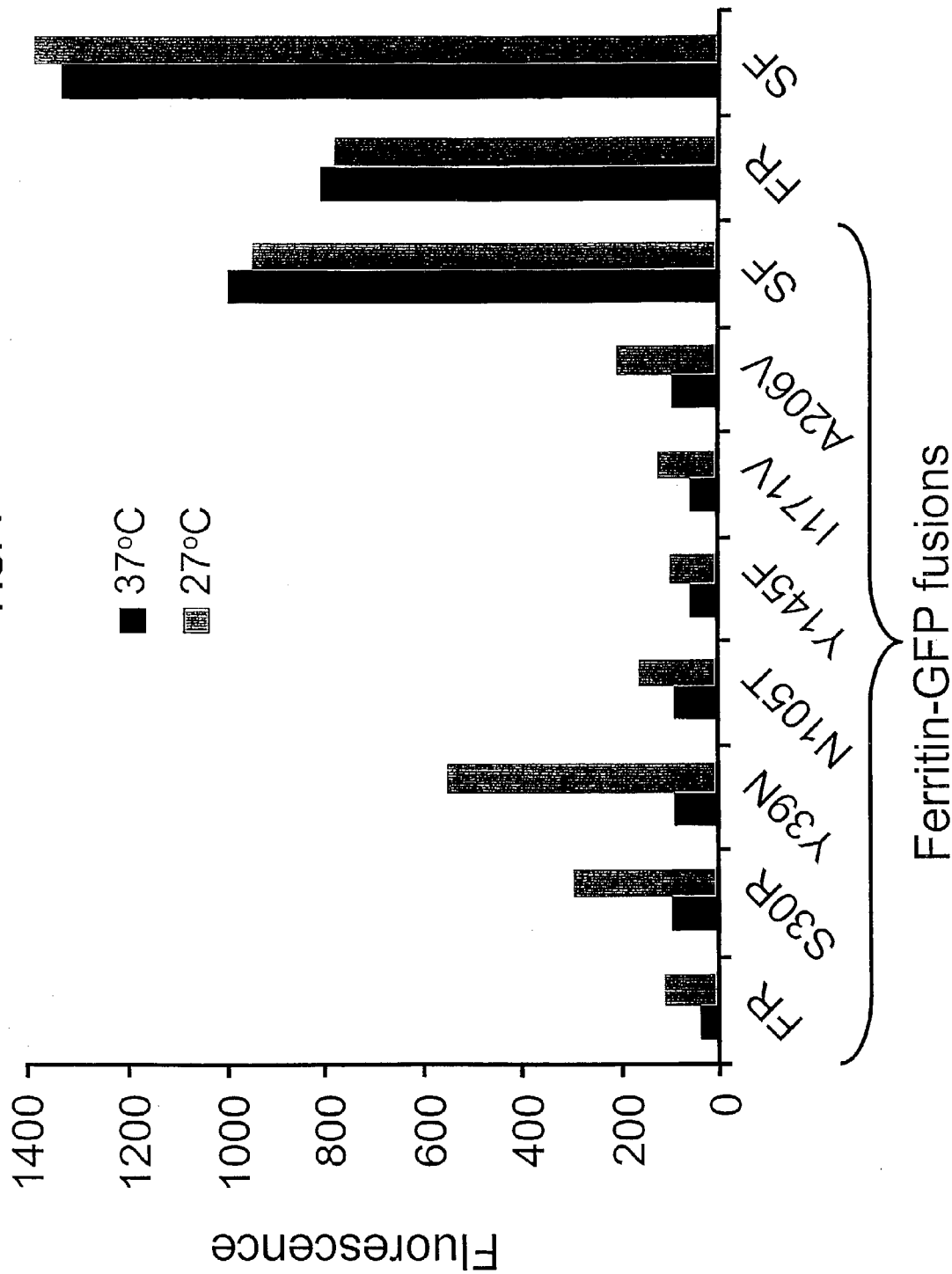
FIG. 1. Normalized whole cell fluorescence for *E. coli* BL21 (DE3) expressing GFP variants as C-terminal fusions with poorly-folded bullfrog red cell H-subunit ferritin (bracketed). Expression at 37° C. (black) and 27° C. (grey). GFP variants (left to right) cycle-3 redshift, 6 single point mutants, super folder (left, bracketed)). Non-fusion GFP variants (cycle-3 redshift and superfolder, (right)) as reference. Note that the fluorescence of the optimized superfolder fused to ferritin is essentially identical to the non-fusion cycle-3 redshift GFP. In contrast, cycle-3 redshift GFP fused to ferritin is poorly folded (far left). As expected, the fluorescence is higher at 27° C. relative to 37° C., consistent with the improved folding at lower temperature.

FIG. 1 shows Normalized whole cell fluorescence for *E. coli* BL21(DE3) expressing GFP variants as C-terminal fusions with poorly-folded bullfrog red cell H-subunit ferritin (bracketed). Expression at 37° C. (black) and 27° C. (grey). GFP variants (left to right) cycle-3 redshift, 6 single point mutants, super folder (left, bracketed)). Non-fusion GFP variants (cycle-3 redshift and superfolder, (right)) as reference. Note that the fluorescence of the optimized superfolder fused to ferritin is essentially identical to the non-fusion cycle-3 redshift GFP. In contrast, cycle-3 redshift GFP fused to ferritin is poorly folded (far left). As expected, the fluorescence is higher at 27° C. relative to 37° C., consistent with the improved folding at lower temperature.

The ferritin-linker-GFPSF fusion protein partitioned quantitatively to the inclusion body fraction, as was the case with the ferritin-linker-GFP3 variant. The solubility of the fusion protein was therefore controlled by the solubility of its most poorly folded domain (ferritin). The aggregated fusion protein also failed to catalyze the oxidation of $Fe^{2+}$, yet was brightly fluorescent. This observation suggested that the aggregated fusion protein still contained a misfolded and poorly soluble ferritin domain, but a correctly folded and functional GFP domain. Accordingly, it was concluded that the superfolder mutations uncoupled the folding of the GFP domain and the formation of the chromophore from the presence of misfolded fused ferritin domain.

Example 2

The following example describes the use of the method of the invention to generate superfolding variants of DsRed.

To create the evolved superfolder dsRED, we followed the same protocol used to create the superfolder GFP (supra) with the following modifications. The starting material was an improved variant of dsRED with decreased aggregation and increased rate of chromophore formation, termed dsRED T4, previously described by Glick and co-workers (Bevis B J, Glick B S. Rapidly maturing variants of the Discosoma red fluorescent protein (DsRed). Nat Biotechnol. 2002 January;20(1):83-87). The starting variant has the dsRED wild-type sequence, with the indicated mutations of Glick (see Table 1).

Clone optima were picked from each round of directed evolution as for GFP, except the IllumaTool (Light Tools Research) was equipped with a 580 nm excitation filter, and the plates were either visually examined or photographed, through a 610 nm long pass red filter. After 5 rounds, the rate of fluorescence increase with each cycle began to reach a plateau (determined by examining the whole-cell culture fluorescence for the pooled top 10 optima from each round in a BioTek FL600 plate reader (580 nm ex/610 nm em, 40)(see FIG. 10). The process was stopped and 10 colonies from round 5 were sequenced. The top 3 brightest colonies all shared the same consensus sequence (see Table 1). Amino acid position 2, which was alanine in the Glick T4 mutant, mutated to glutamic acid in the dsRED superfolder.

A monomeric variant of dsRED was recently engineered by Tsien (Campbell R E, Tour O, Palmer A E, Steinbach P A, Baird G S, Zacharias D A, Tsien R Y. A monomeric red fluorescent protein Proc Natl Acad Sci USA. 002 Jun. 11, 1999(12):7877-82). This sequence is included in Table 1 for reference. The monomeric variant of Tsien contains several of the Glick T4 (this was the starting parental variant used by Tsien & co-workers for engineering the monomeric dsRED). One of the superfolder amino acid positions (177) Was found as F177V by Tsien, and F177I in this work. However, Tsien specified that this mutation was associated with the monomeric character (wild type dsRed is a tetramer). There is no teaching in the work of Tsien that this mutation improves folding above that of the starting variant. F177I in this example, contributing to the improved folding of the dsRED cycle 5, is a new and surprising property of mutation at F177, not anticipated by Tsien. Similarly, the negatively charged R2E of superfolder dsRED cycle 5 in our work differs from the R2A non-charged variant previously described by Glick, and there is no teaching in Glick or Tsien that mutations at R improved the folding of dsRED or increase its tolerance to misfolded fused proteins. Instead, Glick simply states that replacing basic residues near the N-terminus of dsRED can improve its solubility (no statement regarding folding or fluorescence yield). Thus, the property of R2E in increasing the folding yield of dsRED fused to poorly folded proteins is a surprising property of R2.

TABLE 1

Amino acid mutations of various dsRED variants.

| # | aa | dsRED | mdsRED | Glick T4 | sfdsRED based on Glick T4 |
|---|----|-------|--------|----------|---------------------------|
| 1 | 2 | R | A | A | E |
| 2 | 5 | K | E | E | |
| 3 | 6 | N | D | D | |
| 4 | 17 | R | | | H |
| 5 | 21 | T | S | S | |
| 6 | 41 | H | T | T | |
| 7 | 42 | N | Q | | |
| 8 | 43 | T | | | N |
| 9 | 44 | V | A | | |
| 10 | 71 | V | A | | |
| 11 | 83 | K | L | | |
| 12 | 105 | V | | | A |
| 13 | 114 | Q | | | E |
| 14 | 117 | C | E | | |
| 15 | 118 | F | | | L |
| 16 | 124 | F | L | | |
| 17 | 125 | I | R | | |
| 18 | 127 | V | T | | |
| 19 | 145 | A | | P | |
| 20 | 150 | L | M | | |
| 21 | 153 | R | E | | |
| 22 | 156 | V | A | | |
| 23 | 160 | E | | | D |
| 24 | 162 | H | K | | |
| 25 | 163 | K | M | | |
| 26 | 164 | A | R | | |
| 27 | 174 | L | D | | |
| 28 | 175 | V | A | | |
| 29 | 176 | E | | | D |
| 30 | 177 | F | V | | I |
| 31 | 179 | S | T | | |
| 32 | 180 | I | T | | |
| 33 | 192 | Y | A | | |
| 34 | 194 | Y | K | | |
| 35 | 195 | V | T | | |
| 36 | 197 | S | I | | |
| 37 | 203 | S | | | N |
| 38 | 217 | T | A | A | |
| 39 | 222 | H | S | | |
| 40 | 223 | L | T | | |
| 41 | 224 | F | G | | |
| 42 | 225 | L | A | | |

\# index of amino acid cited
aa Position in dsRED amino acid coding sequence of the amino acid cited.
dsRED wild-type amino acid at position cited.
mdsRED amino acid of monomeric variant of Tsien.
Glick T4 amino acid of improved variant of Glick.
sfdsRED amino acid of superfolder dsRED (this work).
Grey rows amino acid positions in common with this work, at which previous workers also specify a mutation relative to wild type.

Example 3

Improved GFP Folding due to Superfolder Mutations

To test the effect of the superfolder mutations in greater detail, 6 single-point mutants of cycle-3 redshift were engineered by PCR using methods well-established in the art. Each mutant incorporated one of the 6 mutations found in the superfolder GFP variant. These were cloned into a pET vector as C-terminal fusions with poorly-folded bullfrog redcell ferritin (Waldo G S, Standish B M, Berendzen J, Terwilliger T C. (1999) Rapid protein-folding assay using green fluorescent protein. Nat. Biotechnol. 17(7): 691-695). Overnight cultures in Luria-Bertani (LB) media containing kanamycin (35 □g.ml$^{-1}$ were diluted 100-fold and grown for 2 h at 37° C. Proteins were expressed for 4 h by adding isopropyl-□-D-thiogalactopyranoside (IPTG) to 1 mM in 3 ml cultures of LB (Luria-Bertani) media at either 37° C. or 27° C. in *E. coli* BL21(DE3) as C-terminal fusions with poorly-folded bullfrog red cell H-subunit ferritin. Cycle-3 redshift and superfolder were cloned and expressed similarly as controls, both with and without the N-terminal ferritin. The fluorescence (488 nm ex/520 nm em) and absorbance (600 nm) were measured for each culture using a BioTek FL-600 plate reader (FIG. 1).

Example 4

Expression and Purification of Cycle-3 and Superfolder GFP Variants

Single colony transformants of either the cycle-3 or superfolder GFP in *E. coli* BL21(DE3) were grown LB, and shaken overnight at 37° C. This pre-culture was used to inoculate LB medium containing kanamycin (35 $\mu g.ml^{-1}$). One colony was picked, inoculated ate a larger volume culture (~1L) that was grown to mid-log phase at 37° C. and subsequently induced with 1 mM IPTG (isopropyl-$\beta$-D-thiogalactopyranoside) for about six hours. The cell pellets were harvested by centrifugation at 5° C. and stored at $-20°$ C.

Cell-free extract was centrifuged (100000 g, 30 min at 15° C.) and the supernatant loaded onto a 10 ml volume metal affinity resin (Talon, Clontech) equilibrated in buffer A (150 mM NaCl, 100 mM Hepes-NaOH pH=7.5). Unbound proteins were washed off with buffer A containing 10 mM imidazole. The bound protein was then eluted with buffer B (200 mM Imidazole, 150 mM NaCl, 100 mM Hepes-NaOH pH=7.5) to a final volume of 15 ml.

Ammonium sulfate was added to 80% saturation (ca. 0.48 mg added to 1 ml of protein solution) at 27° C. The solution was stirred for 15 min at the same temperature until dissolved, then incubated on ice for an additional 30 min. The mixture containing the precipitated protein was centrifuged and the supernatant discarded. The precipitate was progressively dissolved in 3 ml buffer C (20 mM Hepes-NaOH pH=7.5), and the protein solution was dialyzed overnight against the same buffer.

Example 5

Expression of Test Proteins as N-terminal Fusions With GFP

Sixteen proteins from the hyperthermophile *Pyrobaculum aerophilum* that had been previously cloned and characterized, (Waldo G S, Standish B M, Berendzen J, Terwilliger T C. (1999) Rapid protein-folding assay using green fluorescent protein. Nat. Biotechnol. 17(7): 691-695; Waldo G S, (2002) Method for determining and modifying protein/peptide solubility, U.S. Pat. No. 6,448,087, were expressed in *E. coli* BL21(DE3) as N-terminal fusions with either cycle-3 or superfolder GFP. Overnight LB cultures containing kanamycin (35 $\mu g.ml^{-1}$) were diluted 100-fold into fresh 1 ml cultures at 37° C. After 1.5 h, protein expression was induced with 1 mM IPTG at 37° C., then arrested after 45 min by adding chloramphenicol to a final concentration of 100 µg/ml. Cells were pelleted by centrifugation and suspended in buffer D (100 mM TRIS HCl pH 8.0, 150 mM NaCl). Aliquots of these suspended cells were examined for GFP fusion fluorescence and total, protein expression as follows. 10 µl cell aliquots were mixed with 180 µl of buffer D and the fluorescence measured (488 ex/520 em) using an FL600 plate reader (Biotek). 10 µl cell aliquots were mixed with SDS loading buffer containing dithiothreitol in PCR tubes and denatured for 5 min at 95° C. 8 µl of the denatured samples were run on 4-20% gradient gels (BioRad), stained using Gelcode Blue (BioRad), and protein quantified by scanning densitometry using a GS-800 calibrated densitometer (BioRad).

Figure 2:
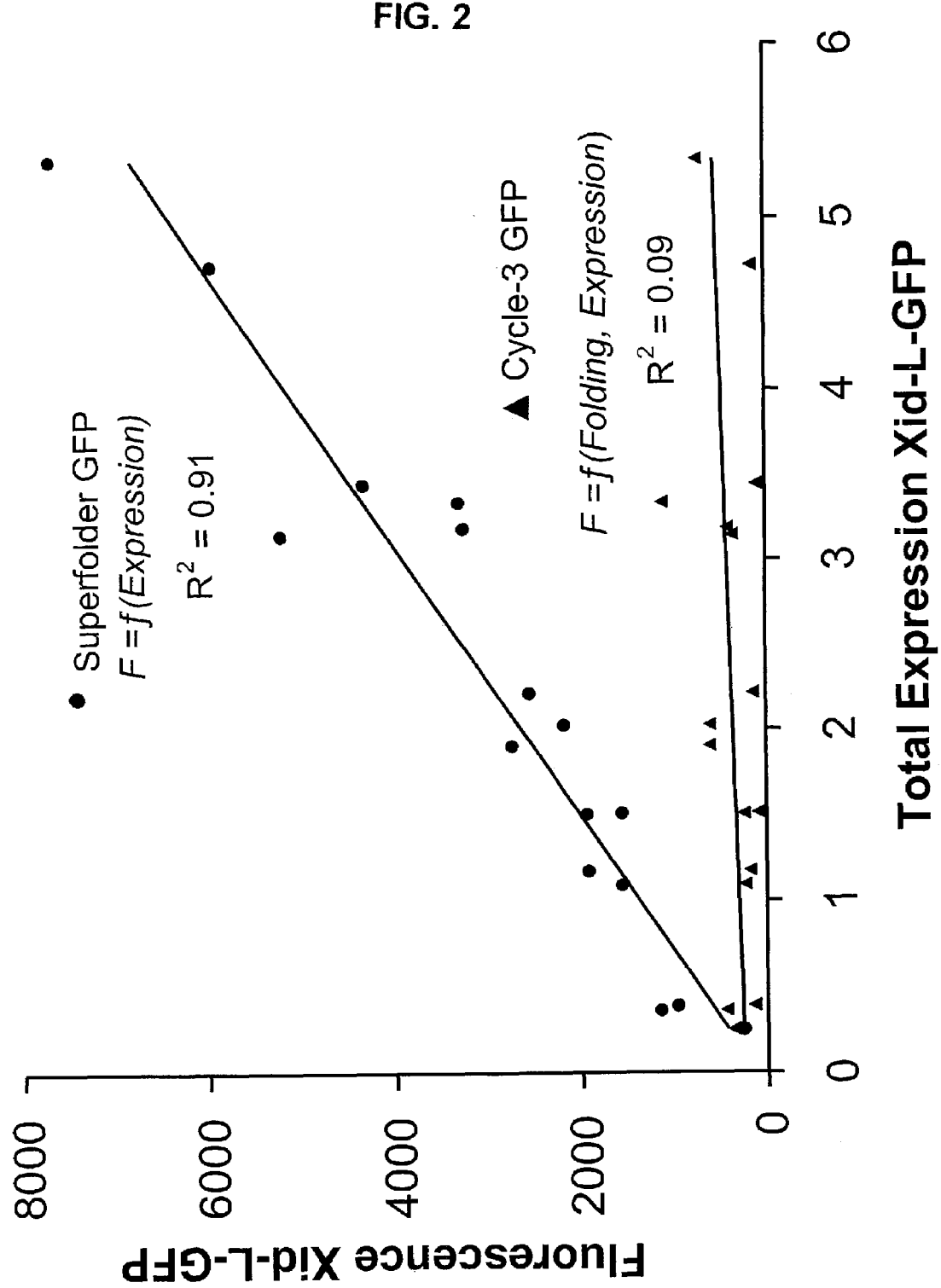
FIG. 2. Proteins from *Pyrobaculum aerophilum* expressed in *Echerichia coli* as N-terminal fusions with either cycle-3 GFP redshift (lower line, triangles) or superfolder GFP (upper line, circles). Sixteen proteins listed in order increasing expression level: tartrate dehydratase beta subunit, nucleoside diphosphate kinase, tyrosine tRNA synthetase, polysulfide reductase subunit, methyltransferase, aspartate-semialdehyde dehydrogenase, purine-nucleoside phosphorylase, soluble hydrogenase, 3-hexulose 6-phosphate synthase, nirD protein, C-type cytochrome biogenesis factor, phosphate cyclase, hydrogenase expression/formation, chorismate mutase, DNA-directed RNA polymerase, and ribosomal protein S9p. Y-axis: whole cell fluorescence (488 nm excitation, 520 nm emission, 10 nm bandpass); X-axis: trace quantity of protein in whole cell fraction determined by SDS-PAGE densitometry.

FIG. 2 represents a plot of the normalized fluorescence versus the total whole cell expression (determined by SDS-PAGE densitometry). Many of the proteins are poorly folded and the cells carrying these constructs are only weakly fluorescent in the case of cycle-3 GFP, as expected. Thus the whole cell fluorescence is poorly correlated with total expression level. Instead, the fluorescence of the cycle-3 GFP fusions was correlated with the non-fusion solubility of the proteins expressed alone as previously reported (Waldo G S, Standish B M, Berendzen J, Terwilliger T C. (1999) Rapid protein-folding assay using green fluorescent protein. Nat. Biotechnol. 17(7): 691-695; Waldo G S, (2002) Method for determining and modifying protein/peptide solubility, U.S. Pat. No. 6,448,087.

In contrast, the fluorescence of the superfolder GFP fusions was overall much higher than that of the cycle-3 GFP fusions (FIG. 2). The fluorescence of the superfolder GFP fusions was well correlated with total expression, suggesting that the folding yield of the GFP domain was independent of the folding yield of the attached upstream protein. Thus, the folding trajectory of the superfolder GFP appears to be considerably more robust than cycle-3 GFP (FIG. 2).

Example 6

Improved Stability of Superfolder GFP to Urea Denaturation

Figure 3:
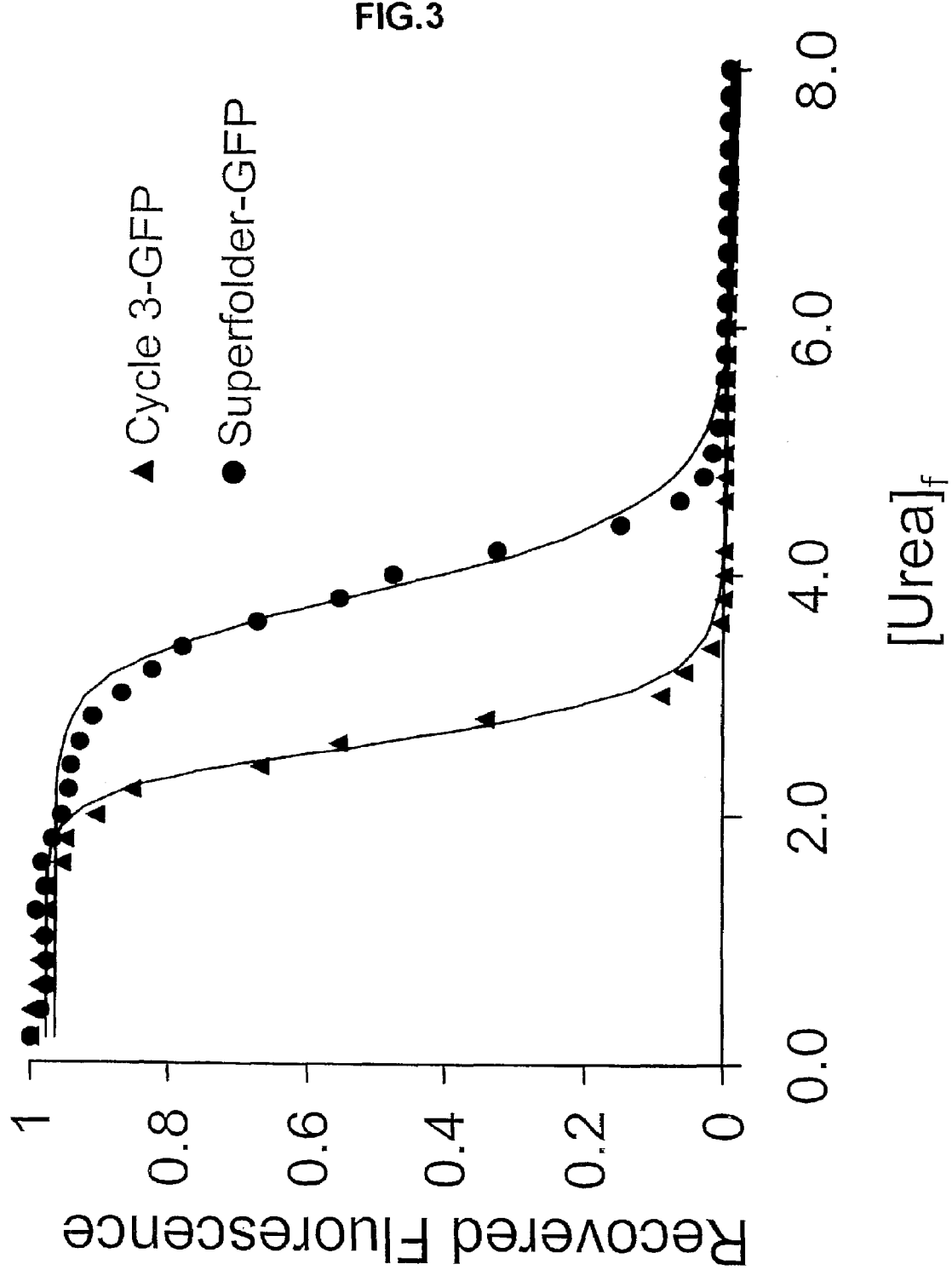
FIG. 3. Tolerance of GFP to urea-induced unfolding during refolding from fully-denatured state. GFP unfolded in 9M urea at 95° C. were refolded by rapidly diluting into TRIS buffer containing the indicated final concentration of urea (x-axis). Cycle-3 redshift (triangles) or superfolder (circles). Fraction of folded protein is determined by fraction of fluorescence recovered (y-axis) at indicated concentration of urea in the refolding buffer (x-axis).

To test the stability of the GFP variants to urea denaturation during refolding, fluorescent GFP was denatured in 9M urea at 95° C. for 5 min until unfolded and non-fluorescent. GFP was renatured (refolded) by rapidly diluting 500-fold in the indicated concentration of urea in 100 mM TRIS pH 7.5, 150 mM NaCl, 10% glycerol, and allowed to refold for 1 h. The fluorescence was measured using a BioTek FL600 plate reader. Equilibrium unfolding concentrations of urea (where 50% of the GFP is folded, 50% unfolded) for superfolder is 3.8 M urea, while for folding reporter (cycle-3 red shift) GFP is 2.4 M, consistent with the improved stability and folding of superfolder (FIG. 3).

Example 7

Improved Refolding Kinetics of Superfolder GFP

Figure 4A:
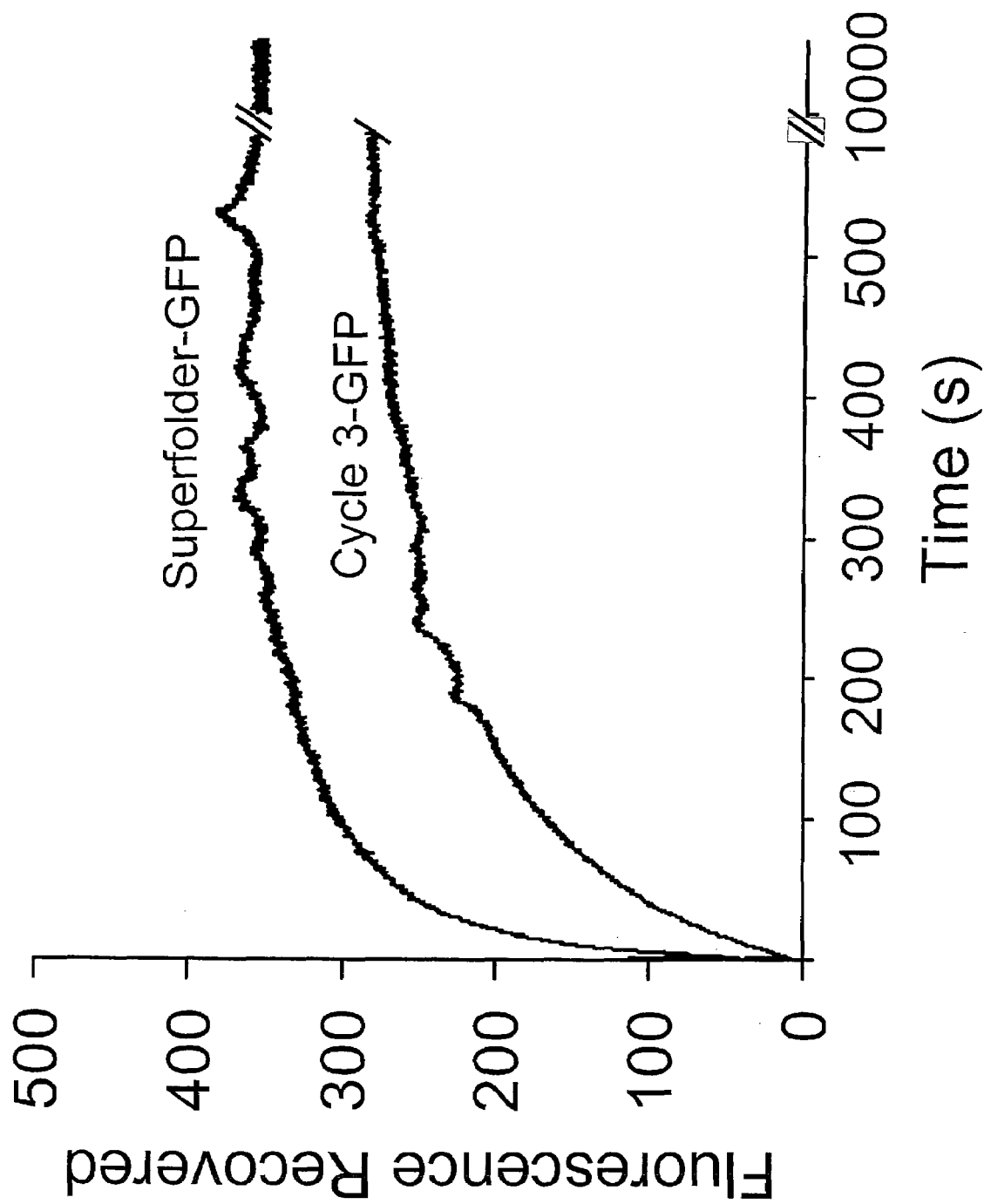
FIG. 4A. Long-term progress curves during refolding of superfolder GFP (SF-GFP) and cycle-3 redshift GFP (C3-GFP). Fully denatured proteins were diluted 100-fold into TRIS buffer (100 mM TRIS-HCl pH 7.5, 150 mM NaCl, 10% v/v glycerol) and the fluorescence measured at 0.2 s intervals with a Perkin Elmer spectrofluorimeter. Note that after 10000 s, both proteins approach the same final value (ca. 375 units).
Figure 4B:
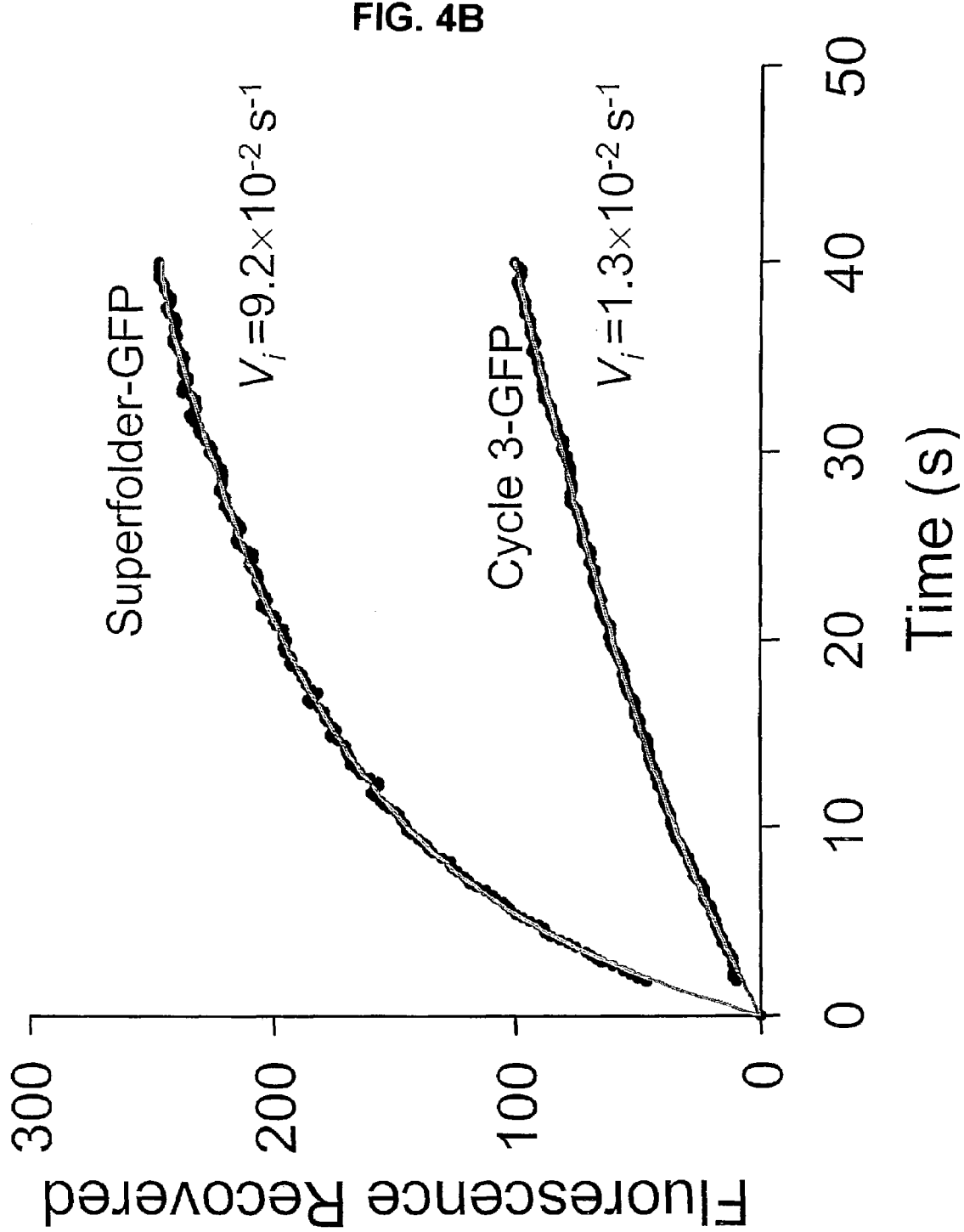
FIG. 4B. Initial rate progress curves during refolding of superfolder GFP (SF-GFP) and cycle-3 redshift GFP (C3-GFP). Fully denatured proteins were diluted 100-fold into TRIS buffer (100 mM TRIS-HCl pH 7.5, 150 mM NaCl, 10% v/v glycerol) and the fluorescence measured at 0.2 s intervals with a Perkin Elmer spectrofluorimeter. Initial rates were determined by fitting a 4th order polynomial to the first 40 s of each progress curve, and converted to pseudo first-order rates by normalizing to the fluorescence at infinite time (ca. 375 units). The superfolder refolds ca. 7 times faster than cycle-3 redshift.

Fluorescent cycle-3 redshift or superfolder GFP were unfolded in 9M urea at 95° C. for 5 minutes until non-fluorescent. The proteins were refolded by diluting 100-fold in 100 mM TRIS pH 7.5, 150 mM NaCl, 10% glycerol, in a rapidly stirred cuvette and the kinetics measured at 0.2 s intervals on a Perkin Elmer spectrofluorimeter (Waldo G S, Standish B M, Berendzen J, Terwilliger T C. (1999) Rapid protein-folding assay using green fluorescent protein. Nat. Biotechnol. 17(7): 691-695). The long-scale kinetics are shown in FIG. 4A. After 10000 s, both superfolder and cycle-3 redshift approached the same final fluorescence values asymptotically (approximation of infinite time), ca. 375 fluorescence units. The initial rates were determined by fitting 4th order polynomials to the first 40 seconds of each progress curve (see FIG. 4B). Rates were normalized to pseudo-first-order rate constants by dividing by the fluorescence values at infinite time (ca. 375). The superfolder refolds approximately 7 times faster than cycle-3 redshift, consistent with the improved folding of superfolder ($9.2 \times 10^{-2} \cdot s^{-1}$ for superfolder, $1.3 \times 10^{-2} s^{-1}$ for cycle-3 redshift This is consistent with the improved folding of superfolder relative to the starting cycle-3 redshift parental variant.

Example 8

Figure 5:
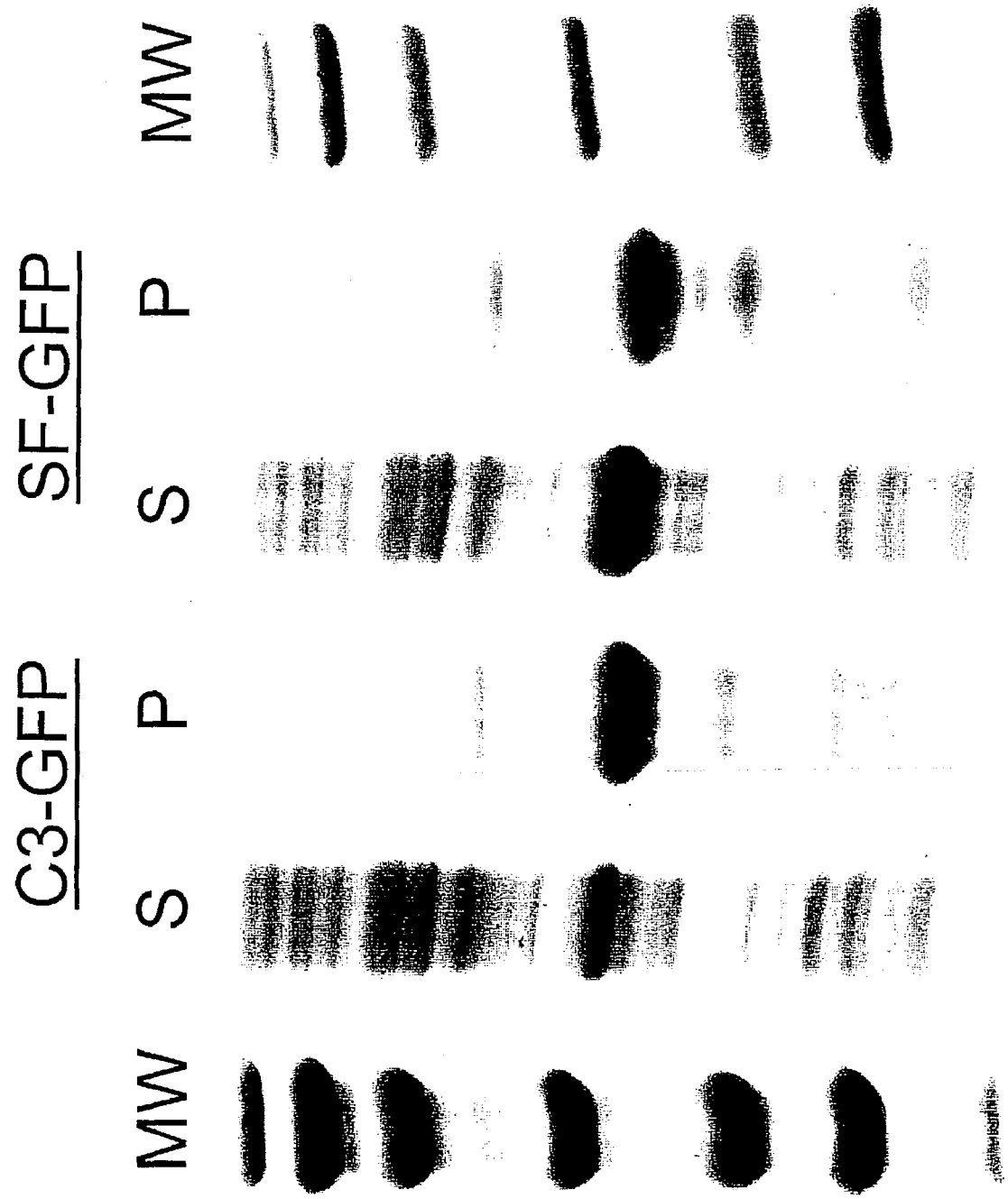
FIG. 5. Increased solubility superfolder mutant pool (right) versus cycle-3 redshift mutant pool (left). SDS-PAGE of (left to right) 10 kD molecular weight standard (M), soluble (S) and pellet (P) fractions of cycle-3 redshift mutant pool (C3-GFP) and superfolder mutant pool (SF-GFP) expressed at 37° C., 10 kD molecular weight standard (M).

Improved Tolerance of Superfolder GFP to Mutations that Normally Decrease the Folding Yield/Solubility of GFP GFP (either cycle-3 redshift or superfolder) was shuffled to create a point mutation rate of ca. 0.7% (Stemmer, W. P. C. (1994). Rapid evolution of a protein in vitro by DNA shuffling. Nature 370, 389-391; Stemmer, W. P. C. (1994). DNA shuffling by random fragmentation and reassembly: In vitro recombination for molecular evolution. PNAS USA 91, 10747-10751). The mutant pools and the starting variants (cycle-3 redshift or superfolder) were expressed in BL21(DE3) at 37° C., sonicated to lysed the cells, fractionated into soluble and pellet fractions by centrifugation, and the soluble and pellet fractions resolved on 20% SDS-PAGE gels, and scanned by densitometer. The starting variants were fully-soluble as expected. In contrast, the mutant pools displayed a significant fraction of misfolded, insoluble protein. Superfolder GFP mutant pool contained ca. 2.5 times the soluble protein of the cycle-3 redshift mutant pool, consistent with the improved folding (and subsequent increased solubility) of the superfolder variant (see FIG. 5).

Example 9

Improved Tolerance of Superfolder GFP to Mutations that Normally Destroy Folding and Fluorescence GFP (either cycle-3 redshift (F64L, S65T) or superfolder) was shuffled to create a point mutation rate of ca. 0.7% (Stemmer, W. P. C. (1994). Rapid evolution of a protein in vitro by DNA shuffling. Nature 370, 389-391; Stemmer, W. P. C. (1994). DNA shuffling by random fragmentation and reassembly: In vitro recombination for molecular evolution. PNAS USA 91, 10747-10751). The mutant pools were expressed in BL21(DE3) at 37° C. and analyzed by flow cytometry. The starting (parental) variants (superfolder or cycle-3 redshift) were cloned and expressed in BL21(DE3) at 37° C. as a standard and analyzed by flow cytometry. The superfolder variant mutant pool has a higher fraction of brighter cells (FIG. 7) compared to the cycle-3 redshift mutant pool (FIG. 6). The increased tolerance of the folding of superfolder GFP to additional random mutations is consistent with the improved folding of the superfolder GFP versus cycle-3 redshift.

Example 10

Improved Tolerance of Superfolder GFP to Circular Permutation

To create the circular permutants, the native N and C termini of each GFP variant were linked by a short GGGS amino acid linker, and new start codons were created at the indicated sites (see Table 2). Sites were chosen to correspond to the middle of loops between structural elements using the published structures of GFP. Manipulation was by primer-based PCR according to standard methods well known in the art. Most proteins do not tolerate circular permutation and still fold (Baird et al., 1999, Proc. Natl. Acad. Sci. USA, 96: 11241-11246). The effect of circular permutation was investigated by studying the solubility of the permutants as well as the fluorescence yield. Circular permutants were cloned into the pET vector equipped with an in-frame Spe-1 and Kpn-1 cloning site as Spe-1/Kpn-1 inserts and expressed in BL21(DE3) at 37° C. for 4 h. The cells were pelleted and fractionated into soluble and pellet fractions according to previously published methods (Waldo G S, Standish B M, Berendzen J, Terwilliger T C. (1999) Rapid protein-folding assay using green fluorescent protein. Nat. Biotechnol. 17(7): 691-695), resolved on SDS-PAGE gels, and the soluble and pellet fractions quantitated by densitometry. Many of the superfolder circular permutants are substantially soluble; in contrast, most of the cycle-3 redshift circular permutants are poorly soluble (see FIG. 8). Fluorescence (480 nm ex/520 nm em) was measured for whole cells in suspension and normalized by dividing by the cell density (optical density 600 nm) (see FIG. 9). As expected, the superfolder is much more tolerant of circular permutation, as evidenced by the greater fluorescence for superfolder compared to cycle-3 redshift for the various circular permutants.

TABLE 2

Primers used to create circular permutants.

| CP | Name | c3 | sf | Name Code | Primer | SEQ ID NO: |
|---|---|---|---|---|---|---|
| a | 2-3 |   | 1 | GFP23+ | GATATAACTAGTAATGGGCACAAATTTTCTGTCAGAGGA | 6 |
| a | 2-3 | 1 |   | GFP23 + wt | GATATAACTAGTAATGGGCACAAATTTTCTGTCAGTGGA | 7 |
| a | 2-3 | 1 | 1 | GFP23- | TACTTCGGTACCATTAACATCACCATCTAATTCAACAAG | 8 |
| b | 3-4 |   | 1 | GFP39+ | GATATAACTAGTAACGGAAAACTCACCCTTAAATTTATT | 9 |
| b | 3-4 | 1 |   | GFP39 + wt | GATATAACTAGTTACGGAAAACTCACCCTTAAATTTATT | 10 |
| b | 3-4 |   | 1 | GFP39- | TACTTCGGTACCGTTTGTAGCATCACCTTCACCCTCTCC | 11 |
| b | 3-4 | 1 |   | GFP39 - wt | TACTTCGGTACCGTATGTAGCATCACCTTCACCCTCTCC | 12 |
| c | chrome 4-3 | 1 | 1 | GFP51+ | GATATAACTAGTGGAAAACTACCTGTTCCATGGCCAACA | 13 |
| c | chrome 4-3 | 1 | 1 | GFP51- | TACTTCGGTACCTCCAGTAGTGCAAATAAATTTAAGGGT | 14 |

TABLE 2-continued

Primers used to create circular permutants.

| CP | Name | c3 | sf | Name Code | Primer | SEQ ID NO: |
|---|---|---|---|---|---|---|
| d | 4-3 | 1 | 1 | GFP91+ | GATATAACTAGTGGTTATGTACAGGAACGCACTATATCT | 15 |
| d | 4-3 | 1 | 1 | GFP91- | TACTTCGGTACCACCTTCGGGCATGGCACTCTTGAAAAA | 16 |
| e | 5-4 |  | 1 | GFP102+ | GATATAACTAGTGATGACGGGACCTACAAGACGCGTGCT | 17 |
| e | 5-4 | 1 |  | GFP102 + wt | GATATAACTAGTGATGACGGGAACTACAAGACGCGTGCT | 18 |
| e | 5-4 | 1 | 1 | GFP102- | TACTTCGGTACCATCTTTGAAAGATATAGTGCGTTCCTG | 19 |
| f | 6-5 | 1 | 1 | GFP117+ | GATATAACTAGTGATACCCTTGTTAATCGTATCGAGTTA | 20 |
| f | 6-5 | 1 | 1 | GFP117- | TACTTCGGTACCATCACCTTCAAACTTGACTTCAGCACG | 21 |
| g | Pre 7-6 | 1 | 1 | GFP129+ | GATATAACTAGTGATTTTAAAGAAGATGGAAACATTCTC | 22 |
| g | Pre 7-6 | 1 | 1 | GFP129- | TACTTCGGTACCATCAATACCTTTTAACTCGATACGATT | 23 |
| h | Pre140 7-6 |  | 1 | GFP140+ | GATATAACTAGTAAACTCGAGTACAACTTTAACTCACAC | 24 |
| h | Pre140 7-6 | 1 |  | GFP140 + wt | GATATAACTAGTAAACTCGAGTACAACTATAACTCACAC | 25 |
| h | Pre140 7-6 | 1 | 1 | GFP140- | TACTTCGGTACCTTTGTGTCCGAGAATGTTTCCATCTTC | 26 |
| i | 7-6 |  | 1 | GFP145+ | GATATAACTAGTTTTAACTCACACAATGTATACATCACG | 27 |
| i | 7-6 | 1 |  | GFP145 + wt | GATATAACTAGTTATAACTCACACAATGTATACATCACG | 28 |
| i | 7-6 |  | 1 | GFP145- | TACTTCGGTACCAAAGTTGTACTCGAGTTTGTGTCCGAG | 29 |
| i | 7-6 | 1 |  | GFP145 - wt | TACTTCGGTACCATAGTTGTACTCGAGTTTGTGTCCGAG | 30 |
| j | 8-7 | 1 | 1 | GFP157+ | GATATAACTAGTCAAAAGAATGGAATCAAAGCTAACTTC | 31 |
| j | 8-7 | 1 | 1 | GFP157- | TACTTCGGTACCTTGTTTGTCTGCCGTGATGTATACATT | 32 |
| k | 9-8 | 1 | 1 | GFP173+ | GATATAACTAGTGATGGTTCCGTTCAACTAGCAGACCAT | 33 |
| k | 9-8 |  | 1 | GFP173- | TACTTCGGTACCATCTTCAACGTTGTGGCGAATTTTGAA | 34 |
| k | 9-8 | 1 |  | GFP173 - wt | TACTTCGGTACCATCTTCAATGTTGTGGCGAATTTTGAA | 35 |
| l | Pre 10-9 | 1 | 1 | GFP189+ | GATATAACTAGTGGCGATGGCCCTGTCCTTTTACCAGAC | 36 |
| l | Pre 10-9 | 1 | 1 | GFP189- | TACTTCGGTACCGCCAATTGGAGTATTTTGTTGATAATG | 37 |
| m | 10-9 | 1 | 1 | GFP195+ | GATATAACTAGTTTACCAGACAACCATTACCTGTCGACA | 38 |
| m | 10-9 | 1 | 1 | GFP195- | TACTTCGGTACCTAAAAGGACAGGGCCATCGCCAATTGG | 39 |
| n | 11-10 | 1 | 1 | GFP214+ | GATATAACTAGTAAGCGTGACCACATGGTCCTTCTTGAG | 40 |
| n | 11-10 |  | 1 | GFP214- | TACTTCGGTACCCTTTTCGTTGGGATCTTTCGAAAGGAC | 41 |
| n | 11-10 | 1 |  | GFP214 - wt | TACTTCGGTACCCTTTTCGTTGGGATCTTTCGAAAGGGC | 42 |

Legend.
CP Single-letter name of each of the 14 circular permutants (a–n).
Name Name of each of the 14 circular permutants cited in FIGS. 9 and 10.
C3 Primer used to make cycle-3 redshift circular permutant variant.
SF Primer used to make superfolder circular permutant variant.
Name Code Code name of primer. Number indicates amino acid of new start codon.
Primer Sequence of primer (5' to 3' sense) used to make circular permutant.

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE OF SEQUENCES
GFP variant nucleotide coding sequence (optimal)
ATGAGCAAAGGAGAAGAACTTTTCACTGGAGTTGTCCCAATTCTTGTTGAATTAG    SEQ ID NO:1

ATGGTGATGTTAATGGGCACAAATTTTCTGTCAGTGGAGAGGGTGAAGGTGATG

CTACATACGGAAAACTCACCCTTAAATTTATTTGCACTACTGGAAAACTACCTGT

TCCATGGCCAACACTTGTCACTACTCTGACCTATGGTGTTCAATGCTTTTCCCGT

TATCCGGATCACATGAAACGGCATGACTTTTTCAAGAGTGCCATGCCCGAAGGT

TATGTACAGGAACGCACTATATCTTTCAAAGATGACGGGAACTACAAGACGCGT

GCTGAAGTCAAGTTTGAAGGTGATACCCTTGTTAATCGTATCGAGTTAAAAGGT

ATTGATTTTAAAGAAGATGGAAACATTCTCGGACACAAACTCGAGTACAACTATA

ACTCACACAATGTATACATCACGGCAGACAAACAAAAGAATGGAATCAAAGCTA

ACTTCAAAATTCGCCACAACATTGAAGATGGTTCCGTTCAACTAGCAGACCATTA

TCAACAAAATACTCCAATTGGCGATGGCCCTGTCCTTTTACCAGACAACCATTAC

CTGTCGACACAATCTGCCCTTTCGAAAGATCCCAACGAAAAGCGTGACCACATG

GTCCTTCTTGAGTTTGTAACTGCTGCTGGGATTACACATGGCATGGATGAGCTC

TACAAATAA

GFP variant amino acid sequence:
MSKGEELFTGVVPILVELDGDVNGHKFSVSGEGEGDATYGKLTLKFICTTGKLPVP    SEQ ID NO:2

WPTLVTTLTYGVQCFSRYPDHMKRHDFFKSAMPEGYVQERTISFKDDGNYKTRAE

VKFEGDTLVNRIELKGIDFKEDGNILGHKLEYNYNSHNVYITADKQKNGIKANFKIRH

NIEDGSVQLADHYQQNTPIGDGPVLLPDNHYLSTQSALSKDPNEKRDHMVLLEFVT

AAGITHGMDELYK*

DsRed<sub>SF</sub> variant nucleotide coding sequence:
ATGGAGTCTTCCGAGGATGTTATCAAGGAGTTCATGAGGTTTAAGGTTCACATG    SEQ ID NO:3

GAAGGATCGGTCAATGGGCACGAGTTTGAAATAGAAGGCGAAGGAGAGGGGA

GGCCATACGAAGGCACCCAGAACGTAAAGCTTAAGGTAACTAAGGGGGGACCT

TTGCCATTTGCTTGGGATATTTTGTCACCACAATTTCAGTATGGAAGCAAGGTAT

ATGTCAAGCACCCTGCCGACATACCAGACTATAAAAAGCTGTCATTTCCTGAAG

GATTTAAATGGGAAAGGGTCATGAACTTTGAAGACGGTGGCGTCGCTACTGTAA

CCCAGGATTCCAGTTTGGAGGATGGCTGTTTGATCTACAAGGTCAAGTTCATTG

GCGTGAACTTTCCTTCCGATGGACCTGTTATGCAAAAGAAGACAATGGGCTGG

GAACCGAGCACTGAGCGTTTGTATCCTCGTGATGGCGTGTTGAAAGGAGATATT

CATAAGGCTCTGAAGCTGAAAGACGGTGGTCATTACCTAGTTGATATCAAAAGT

ATTTACATGGCAAAGAAGCCTGTGCAGCTACCAGGGTACTACTATGTTGACTCC

AAACTGGATATAACAAACCACAACGAAGACTATACAATCGTTGAGCAGTATGAA

AGAGCCGAGGGACGCCACCATCTGTTCCTTTAA

DsRed<sub>SF</sub> variant amino acid sequence:
MESSEDVIKEFMRFKVHMEGSVNGHEFEIEGEGEGRPYEGTQNVKLKVTKGGPLP    SEQ ID NO:4

FAWDILSPQFQYGSKVYVKHPADIPDYKKLSFPEGFKWERVMNFEDGGVATVTQD

SSLEDGCLIYKVKFIGVNFPSDGPVMQKKTMGWEPSTERLYPRDGVLKGDIHKALK

LKDGGHYLVDIKSIYMAKKPVQLPGYYYVDSKLDITNHNEDYTIVEQYERAEGRHHL

FL

-continued

Wild type GFP amino acid sequence
(Swiss protein database accession P42212):
MSKGEELFTGVVPILVELDGDVNGHKFSVSGEGEGDATYGKLTLKFICTTGKLPVP    SEQ ID NO:5

WPTLVTTFSYGVQCFSRYPDHMKQHDFFKSAMPEGYVQERTIFFKDDGNYKTRAE

VKFEGDTLVNRIELKGIDFKEDGNILGHKLEYNYNSHNVYIMADKQKNGIKVNFKIRH

NIEDGSVQLADHYQQNTPIGDGPVLLPDNHYLSTQSALSKDPNEKRDHMVLLEFVT

AAGITHGMDELYK

---

What is claimed is:

1. A green fluorescent protein that has:
   (a) at least 80% Identity to SEQ ID NO:2;
   (b) at least one amino acid substitution selected from the group consisting of a substitution at position 30 that is an arginine or a conservative variant of arginine; a substitution at position 39 that is an asparagine or a conservative variant of asparagine; a substitution at position 105 that is a threonine or a conservative variant of threonine; a substitution at position 171 that is a valine; and a substitution at position 206 that is a valine; wherein the positions are determined in alignment for maximal correspondence with SEQ ID NO:2; and
   (c) measurable fluorescence activity.

2. A green fluorescent protein of claim 1, further comprising a phenylalanine substitution at position 145.

3. A green fluorescent protein of claim 1, wherein the amino acid substitution is selected from the group consisting of an arginine substitution at position 30; an asparagine substitution at position 39; a threonine substitution at position 105; a valine substitution at position 171; and a valine substitution at position 206.

4. A green fluorescent protein of claim 1, wherein the substitution is an arginine at position 30.

5. A green fluorescent protein of claim 1, wherein the substitution is an asparagine at position 39.

6. A green fluorescent protein of claim 1, wherein the substitution is a threonine at position 105.

7. A green fluorescent protein of claim 1, wherein the substitution is a phenylalanine at position 145.

8. A green fluorescent protein of claim 1, wherein the substitution is a valine at position 171.

9. A green fluorescent protein of claim 1, wherein the substitution is a valine at position 206.

10. A green fluorescent protein of claim 1, wherein the green fluorescent protein comprises two substitutions selected from the group set forth in claim 1.

11. A green fluorescent protein of claim 1, wherein the green fluorescent protein comprises three substitutions selected from the group set forth in claim 1.

12. A green fluorescent protein of claim 1, wherein the green fluorescent protein comprises four substitutions selected from the group set forth in claim 1.

13. A green fluorescent protein of claim 1, wherein the green fluorescent protein comprises five substitutions selected from the group set forth in claim 1.

14. A green fluorescent protein of claim 13, wherein the five substitutions are an arginine at position 30, an asparagine at position 39, a threonine at position 105, a valine at position 171, and a valine at position 206.

15. A green fluorescent protein of claim 14, wherein the green fluorescent protein further comprises a sixth substitution that is a phenylalanine at position 145.

16. A green fluorescent protein of claim 15, further comprising a mutation selected from the group consisting of F99S, M153T, and V163A.

17. A green fluorescent protein of claim 15, further comprising mutations F99S, M153T and V163A.

18. A green fluorescent protein of claim 1, wherein the protein is cyclized.

* * * * *